(12) United States Patent
Richt et al.

(10) Patent No.: US 10,881,722 B2
(45) Date of Patent: Jan. 5, 2021

(54) EPIZOOTIC HEMORRHAGIC DISEASE VACCINE

(71) Applicants: Kansas State University Research Foundation, Manhattan, KS (US); The United States of America, as represented by The Secretary of Agriculture, Washington, DC (US)

(72) Inventors: Juergen A. Richt, Manhattan, KS (US); Igor Morozov, Manhattan, KS (US); Sun Young Sunwoo, Manhattan, KS (US); William C. Wilson, Manhattan, KS (US)

(73) Assignees: Kansas State University Research Foundation, Manhattan, KS (US); The United States of America, as reoresented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 16/334,885

(22) PCT Filed: Sep. 18, 2017

(86) PCT No.: PCT/US2017/052084
§ 371 (c)(1),
(2) Date: Mar. 20, 2019

(87) PCT Pub. No.: WO2018/057467
PCT Pub. Date: Mar. 29, 2018

(65) Prior Publication Data
US 2020/0016259 A1    Jan. 16, 2020

Related U.S. Application Data

(60) Provisional application No. 62/397,265, filed on Sep. 20, 2016.

(51) Int. Cl.
| | | |
|---|---|---|
| *A61K 35/76* | (2015.01) | |
| *A61K 39/12* | (2006.01) | |
| *C07K 14/08* | (2006.01) | |
| *C12N 15/86* | (2006.01) | |
| *C12N 7/00* | (2006.01) | |
| *A61K 39/00* | (2006.01) | |

(52) U.S. Cl.
CPC .............. *A61K 39/12* (2013.01); *C07K 14/08* (2013.01); *C12N 15/86* (2013.01); *A61K 2039/5252* (2013.01); *A61K 2039/55566* (2013.01); *C12N 2720/12134* (2013.01)

(58) Field of Classification Search
CPC ......... A61P 31/14; A61K 39/12; A01N 59/02; Y10S 530/826; C07K 2317/31; C12N 2720/12134; C12N 9/1252; C12N 9/1276; C12N 2740/16134; G01N 33/6872; G01N 33/56983
See application file for complete search history.

(56) References Cited

U.S. PATENT DOCUMENTS

2001/0033845 A1    10/2001    Ganne

OTHER PUBLICATIONS

Alshaikhahmed et al., Generation of virus-like particles for emerging epizootic haemorrhagic disease virus: Towards the development of safe vaccine candidates. Vaccine, Feb. 17 2016, vol. 34 No. 8, pp. 1103-1108.
GenBank Accession No. AM744998.1. Epizootic hemorrhagic disease virus (serotype 2 / strain Alberta) segment 2. Mar. 7, 2015 (retrieved Nov. 18, 2017).
GenBank Accession No. AM745002.1. Epizootic hemorrhagic disease virus (serotype 2 / strain Alberta) segment 6. Mar. 7, 2015 (retrieved Nov. 18, 2017).
Anthony et al., Genetic and phylogenetic analysis of the outer-coat proteins VP2 and VP5 of epizootic haemorrhagic disease virus (EHDV): Comparison of genetic and serological data to characterise the EHDV serogroup. Virus Research, Nov. 2009, vol. 145 No. 2, pp. 200-210.

*Primary Examiner* — Bao Q Li
(74) *Attorney, Agent, or Firm* — Tracey S. Truitt; Armstrong Teasdale LLP

(57) ABSTRACT

The present disclosure provides for an immunogenic composition against epizootic hemorrhagic disease virus (EHDV). The immunogenic composition has been shown to be efficacious in inducing serum neutralizing antibodies against EHDV and intended to be used to prevent or reduce clinical symptoms associated with EHDV infection in susceptible animals. The disclosure provides for composition and methods that represent an improvement over previous strategies for treating and preventing EHDV.

16 Claims, 8 Drawing Sheets
Specification includes a Sequence Listing.

EPIZOOTIC HEMORRHAGIC DISEASE VACCINE

CROSS REFERENCE TO RELATED APPLICATIONS

The present application claims priority to U.S. Patent Application No. 62/397,265, filed on Sep. 20, 2016, which is hereby incorporated by reference in its entirety.

BACKGROUND OF THE INVENTION

Epizootic hemorrhagic disease (EHD) is a vector-borne viral disease of wild and domestic ruminants. EHD virus (EHDV) infection causes severe clinical signs and high mortality in wild ruminants, especially in white-tail deer (WTD), which is the most susceptible species, and can also cause disease in domestic cattle. The disease is economically important for deer and cattle farmers due to the loss of animals and restrictions on trading livestock. Recent concerns about EHDV were caused by the expansion of the affected area and the emergence of serotype 6 in the US. Serotype 6 was isolated from dead WTD in 2006 and was also found to be responsible for morbidity and mortality in cattle.

Autogenous inactivated vaccines have been used for protection of EHDV infection in North America. There are several steps to make an autogenous vaccine including virus isolation, confirmation of identity, propagation of virus, virus inactivation and proof of virus inactivation, USDA-required safety and purity testing, as well as approval by government authorities. These autogenous vaccines are primarily if not solely used by deer farmers. In Japan, both live modified and inactivated vaccines have been developed to control Ibaraki disease caused by an EHDV-2 strain. Autogenous inactivated vaccines have several limitations: the process needs approximately 12 weeks before delivery to the farm, inability to differentiate between vaccination and infection in the serological test, limitation of protection only to the homologous serotype and vaccine side effects caused by whole inactivated virus/adjuvant.

BRIEF DESCRIPTION OF THE INVENTION

The present disclosure provides for an immunogenic composition or vaccine against EHD. Further, a method for eliciting an immune response in an animal is provided, where the steps include administration of the immunogenic composition or vaccine disclosed herein to an animal in need thereof. A method for reducing the incidence and/or severity of clinical signs associated with EHD, as well as a method of reducing viremia is also provided as an aspect of the disclosure. Such a method comprises the steps of administration of the immunogenic composition or vaccine disclosed herein to an animal in need thereof.

In one aspect, the immunogenic composition or vaccine of the present disclosure is preferably a protein subunit or DNA-based. In a preferred embodiment, the protein subunit is selected from VP1, VP2, VP3, VP4, VP5, VP6, VP7, NS1, NS2, NS3a, NS3b, NS4 and any combination thereof as well as the DNA sequences encoding such subunits. In a preferred aspect, the protein subunit is selected from VP2, VP5 and combinations thereof. In some forms, the protein subunits are recombinantly produced.

The recombinant protein-based vaccine or immunogenic composition utilizes selected immune-dominant proteins as antigens to ensure protection of vaccinates from virus infection. The immunogenic composition of the present disclosure preferably includes at least one VP2 structural protein of EHDV-2 or other EHDV serotype. In preferred forms, VP2 and VP5 structural proteins are used, where the VP2 structural protein can be from more than one EHDV serotype and the VP5 structural protein can be from more than on EHDV serotype. In its most preferred form, structural proteins of multiple EHDV serotypes are included in the immunogenic composition or vaccine. VP2 and VP5 are major structural proteins involved in virus attachment and entry into the host cell. They are also major targets for neutralizing antibodies. The recombinant protein vaccines used in this application revealed specific serological reactivity and neutralizing activity against EHD virus. This disclosure demonstrates that a combination of VP2 and VP5 protein subunits induces neutralizing antibodies associated with protection against EHDV infection, although the immunogenic composition is not so limited. The examples contained in this disclosure also demonstrated that immunization with the VP2 protein subunit alone stimulates production of EHDV-specific neutralizing antibodies and leads to protection from EHDV infection, although the immunogenic composition is not so limited. The use of recombinant proteins which are safe and protective is an advantage over the previous methods.

In one aspect, the immunogenic composition of the present disclosure using recombinant protein doesn't use the live EHDV during all processes, so it does not require propagation of infectious virus and virus inactivation steps. The immunogenic composition or vaccine of the present disclosure can be used to prevent EHDV infection and spread in cattle and deer, and is DIVA (differentiating infected from vaccinated animals) compatible, which is an important feature for the control of the disease.

In another aspect, the immunogenic composition comprises a DNA vector plasmid capable of expressing the protein subunits in vivo. The vector or plasmid may also contain an acceptable pharmaceutical or veterinary vehicle. In a preferred aspect, the plasmid or vector comprises a nucleotide sequence of the genome of EHDV, a subunit, a homologue, or fragment thereof. In one aspect, the immunogenic composition or vaccine further comprises a gene coding for an expression product capable of inhibiting or retarding the establishment or development of a virus. Preferred nucleotide sequences include those encoding VP1, VP2, VP3, VP4, VP5, VP6, VP7, NS1, NS2, NS3a, NS3b, NS4 and any combination thereof.

BRIEF DESCRIPTION OF THE DRAWINGS

FIG. 1 is Western blot of recombinant VP2 and VP5 proteins of EHDV2 and EHDV6. VP5 recombinant proteins revealed a band of about 60 kDa and VP2 proteins revealed a band of about 115 kDa in a western blot using anti-histidine tag-HRP antibody;

FIG. 2 is a graph illustrating specific OD values of sera from immunized mice against VP2/EHDV2 protein (*=$p<0.05$);

FIG. 7 is a graph illustrating Virus Neutralization titers of sera from immunized mice against EHDV2 virus at 35 dpv;

FIG. 8 is a graph illustrating Virus Neutralization titers of sera from mice immunized with recombinant proteins against EHDV serotype 6 virus;

FIG. 9 is a graph illustrating Virus Neutralization titers of sera against EHDV6 virus at 35 dpv;

FIG. 10 is a graph illustrating specific OD values of serum from immunized cattle against the VP2/EHDV2 protein;

Figures 11, 12:
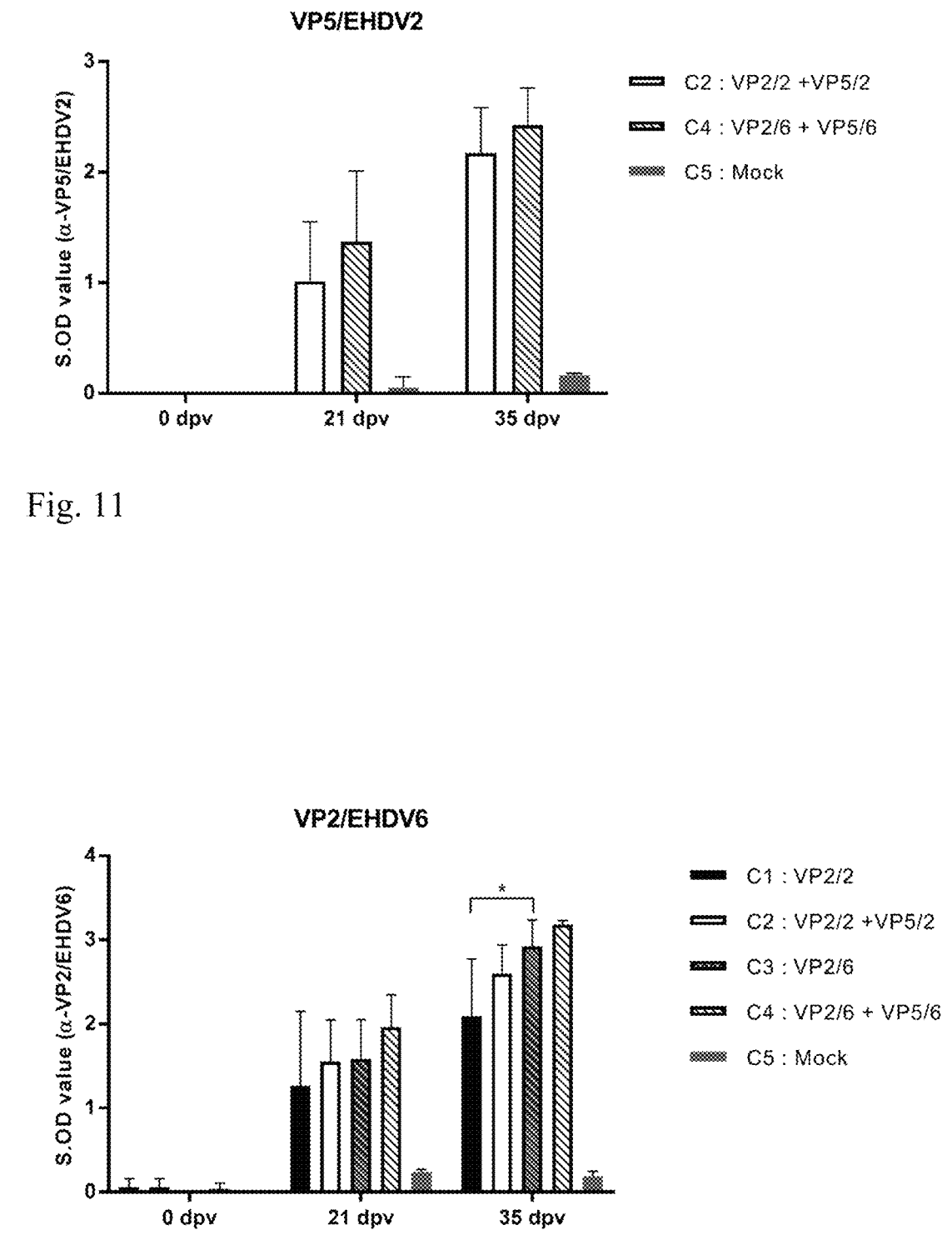

FIG. 11 is a graph illustrating specific OD values of serum from immunized cattle against the VP5/EHDV2 protein;

FIG. 12 is a graph illustrating specific OD values of serum from immunized cattle against VP2/EHDV 6 proteins;

FIG. 13 is a graph illustrating specific OD values of serum from immunized cattle against the VP5/EHDV 6 protein (*=p<0.05); and FIG. 14 is a graph illustrating a specific Virus Neutralization titers of serum against EHDV 2 virus at 35 dpv. The individual Virus Neutralization titer presents with mean of respective group with standard deviation.

DETAILED DESCRIPTION OF THE INVENTION

Figure 3:
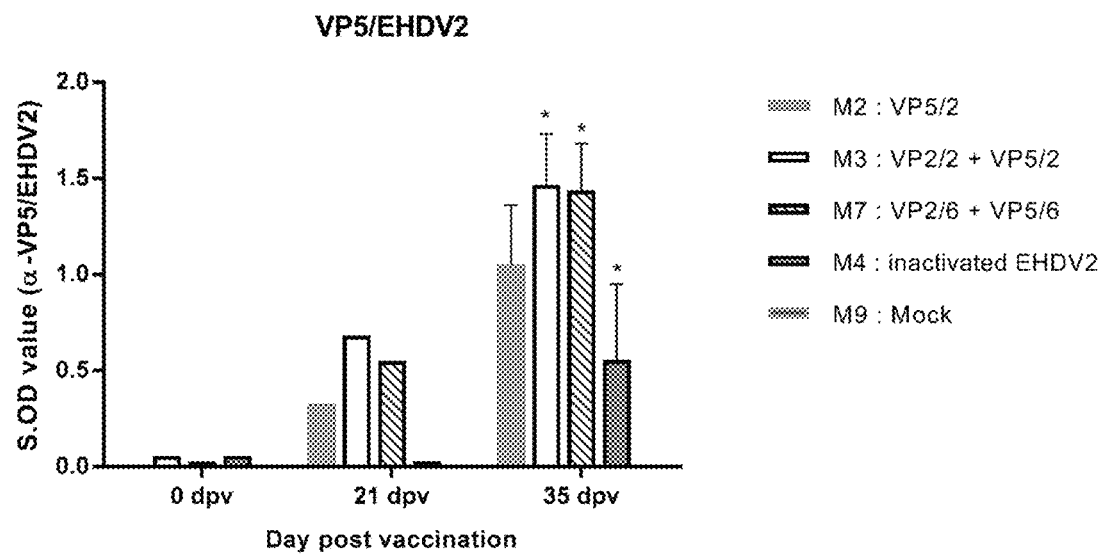
FIG. 3 is a graph illustrating specific OD values of sera from immunized mice against VP5/EHDV2 proteins (*=$p<0.05$)

The present disclosure provides for an immunogenic composition or vaccine providing protection against EHDV. The immunogenic composition or vaccine is preferably protein subunit-based or DNA/RNA-based.

In one aspect, the immunogenic composition or vaccine is a subunit immunogenic composition or vaccine. The subunit is preferably selected from, but not limited to, VP1, VP2, VP3, VP4, VP5, VP6, VP7, NS2, NS3, and any combination thereof. The protein subunits are preferably purified and isolated. The immunogenic composition or vaccine may include 1, 2, 3, 4, 5, 6, 7, 8, 9 or 10 subunits, where each subunit may be the same or different. In one aspect, the combination of subunits may be two or more of the same subunits from different strains or serotypes of EHDV. In another aspect, the selected protein subunits could all be from the same strain or serotype of EHDV. Preferred combinations include, but are not limited to, VP2 from one serotype, VP2 of different serotypes, VP5 of one serotype, VP5 of different serotypes, VP2 and VP5 from one serotype or VP2 and VP5 of different serotypes. As a non-limiting example, the immunogenic composition of the present disclosure may comprise a VP2 from EHDV-1, a VP2 from EHDV-2 and/or the VP2 from EHDV-6. In one aspect, the serotype that the VP2 is derived from determines the serotype of EHDV the vaccine is protective for. The subunits for use in the immunogenic composition or vaccine of the present disclosure are preferably selected from, but not limited to, EHDV-1, EHDV-2, EHDV-6, EHDV-7, or other EHDV serotypes.

The subunits for purposes of the present disclosure are preferably proteins that are recovered after being produced by a protein expression system. In a preferred aspect, the proteins are produced using a baculovirus expression system; however, the disclosure is not so limited. In a preferred aspect the baculovirus expression system is an insect baculovirus expression system. Other expression systems that may be used include mammalian, bacterial, or yeast or protein expression systems.

The nucleic acid sequences encoding for the subunits for use with the present disclosure may also be utilized in the form of DNA or RNA in the immunogenic composition or vaccine.

The EHDV serotype 2 strain for purposes of the present disclosure may be any serotype 2 EHDV strain. Preferably, the EHDV serotype 2 strain is isolated and purified. In one aspect, the protein subunits for use in the immunogenic composition or vaccine is from an EHDV serotype 2 strain having at least 95% sequence homology with the Alberta EHDV serotype 2 strain where values such as at least 96% sequence homology, at least 97% sequence homology, at least 98% sequence homology, and at least 99% sequence homology are envisioned. The proteins utilized in some aspects of the present disclosure are those proteins expressed by sequences having at least 95% sequence homology with proteins of EHDV strain Alberta where values such as at least 96% sequence homology, at least 97% sequence homology, at least 98% sequence homology, and at least 99% sequence homology are envisioned. For purposes of this disclosure the Alberta strain an EHDV2 consisting of 10 segments, GenBank Accession No. AM744997.1 for VP1; GenBank Accession No. AM744998.1 for VP2; GenBank Accession No. AM744999.1 for VP3; GenBank Accession No. AM745000.1 for VP4; GenBank Accession No. AM745001.1 for NS1; GenBank Accession No. AM7745002.1 for VP5; GenBank Accession No. AM745003.1 for VP7; GenBank Accession No. AM745004.1 for NS2; GenBank Accession No. AM745005.1 for VP6; and GenBank Accession No. AM745006.1 for NS3&3a.

The EHDV serotype 1 strain for purposes of the present disclosure may be any serotype 1 EHDV strain. The EHDV serotype 1 strain is preferably purified and isolated. In one aspect, the protein subunits for use in the immunogenic composition or vaccine are from an EHDV serotype 1 strain having at least 95% sequence homology with the EHDV1/NJ serotype 1 strain where values such as at least 96% sequence homology, at least 97% sequence homology, at least 98% sequence homology, and at least 99% sequence homology are envisioned. The proteins utilized in some aspects of the present disclosure are those proteins expressed by sequences having at least 95% sequence homology with nucleic acid sequences of EHDV1/NJ strain where values such as at least 96% sequence homology, at least 97% sequence homology, at least 98% sequence homology, and at least 99% sequence homology are envisioned. For purposes of this disclosure the EHDV1/NJ strain consists of the following 10 segments: GenBank Accession No. KU140704.1 for VP1; GenBank Accession No. KU140740.1 for VP2; GenBank Accession No. KU140752.1 for VP3; GenBank Accession No. KU140776.1 for VP4; GenBank Accession No. KU140800.1 for NS1; GenBank Accession No. KU1407836.1 for VP5; GenBank Accession No. KU140872.1 for VP7; GenBank Accession No. KU140848.1 for NS2; GenBank Accession No. KU140896.1 for VP6; and GenBank Accession No. KU140920.1 for NS3&3a.

The EHDV serotype 6 strain for purposes of the present disclosure may be any serotype 6 EHDV strain. The EHDV serotype 6 strain is preferably purified and isolated. In one aspect, the EHDV serotype 6 strain has at least 95% sequence homology with US EHDV6 isolate C/cervidae/

Ohio/12-3437-8/2012, where values such as at least 96% sequence homology, at least 97% sequence homology, at least 98% sequence homology, and at least 99% sequence homology are envisioned. The proteins utilized in some aspects of the present disclosure are those proteins expressed by sequences having at least 95% sequence homology with US EHDV6 isolate C/cervidae/Ohio/12-3437-8/2012 where values such as at least 96% sequence homology, at least 97% sequence homology, at least 98% sequence homology, and at least 99% sequence homology are envisioned. For purposes of the present disclosure, EHDV6 isolate C/cervidae/Ohio/12-3437-8/2012 has 10 segments: GenBank Accession No. KF570133.1 for VP1; GenBank Accession No. KF570134.1for VP2; GenBank Accession No. KF570135.1 for VP3; GenBank Accession No. KF570136.1for VP4; GenBank Accession No. KF570137.1 for VP5; GenBank Accession No. KF570138.1for VP6; GenBank Accession No. KF570139.1 for VP7; GenBank Accession No. KF570140.1 for NS1; GenBank Accession No. KF570141.1 for NS2; and GenBank Accession No. KF570142.1 for NS3&3a.

In a further aspect, the EHDV strain is preferably a strain having at least 95% sequence homology, at least 96% sequence homology, at least 97% sequence homology, at least 98% sequence homology, or at least 99% sequence homology with VP2 and VP5 genes of the Alberta strain of EHDV2 (Genbank #AM744998.1 for VP2 and AM745002.1 for VP5) or a strain having at least 95% sequence homology, at least 96% sequence homology, at least 97% sequence homology, at least 98% sequence homology, or at least 99% sequence homology with VP2 and VP5 genes the US EHDV6 isolate C/cervidae/Ohio/12-3437-8/2012 (GenBank Accession No. KF570134.1 for VP2 and KF570137.1 for VP5). The proteins utilized in some aspects of the present disclosure are those proteins expressed by sequences having at least 95% sequence homology, at least 96% sequence homology, at least 97% sequence homology, at least 98% sequence homology, or at least 99% sequence homology with the Alberta strain of EHDV2 or a strain having at least 95% sequence homology, at least 96% sequence homology, at least 97% sequence homology, at least 98% sequence homology, or at least 99% sequence homology with the US EHDV6 isolate C/cervidae/Ohio/12-3437-8/2012. In a preferred aspect, the EHDV strain is purified and/or isolated.

The VP5 subunit for purposes of the present disclosure may be any VP5 from any stain of EHDV. The VP5 subunit protein is preferably isolated and/or purified. In one aspect, the VP5 subunit is the protein expressed by a sequence having at least 80% nucleotide sequence homology to SEQ ID No. 2 or SEQ ID No. 4, where values such as at least 85%, at least 85%, at least 87%, at least 88%, at least 89%, at least 90%, at least 91%, at least 92%, at least 93%, at least 94%, at least 95%, at least 96%, at least 97%, at least 98%, and at least 99% sequence homology are envisioned. In yet another aspect, the VP5 subunit is a protein having an amino acid sequence that has at least 80% sequence homology to SEQ ID No. 6 or SEQ ID No. 7, where values such as at least 85%, at least 85%, at least 87%, at least 88%, at least 89%, at least 90%, at least 91%, at least 92%, at least 93%, at least 94%, at least 95%, at least 96%, at least 97%, at least 98%, and at least 99% sequence homology are envisioned.

The VP5 subunit may come from any one or more of EHDV-1, EHDV-2 and EHDV-6 serotypes, where the immunogenic composition or vaccine of the present disclosure may include one or more VP5 subunits.

In a further aspect the VP5 subunit for purposes of the present disclosure is the protein expressed by a sequence having at least 95% sequence homology, at least 96% sequence homology, at least 97% sequence homology, at least 98% sequence homology, or at least 99% sequence homology with Gen Bank Accession #AM745002.1 and/or Gen Bank Accession #KF570137.1.

In yet another aspect, the VP2 subunit for purposes of the present disclosure is the protein expressed by a sequence having at least 95% sequence homology, at least 96% sequence homology, at least 97% sequence homology, at least 98% sequence homology, or at least 99% sequence homology with Gen Bank Accession #AM744998.1 and/or Gen Bank Accession #KF570134.1. The VP2 subunit protein is preferably isolated and/or purified.

The VP2 subunit for purposes of the present disclosure may be any VP2 from any stain of EHDV. In one aspect, the VP2 subunit is the protein expressed by a sequence having at least 80% sequence homology to SEQ ID No. 1 or SEQ ID No. 3, where values such as at least 85%, at least 85%, at least 87%, at least 88%, at least 89%, at least 90%, at least 91%, at least 92%, at least 93%, at least 94%, at least 95%, at least 96%, at least 97%, at least 98%, and at least 99% sequence homology are envisioned. In another aspect, the VP2 subunit is a protein having an amino acid sequence that has at least 80% sequence homology to SEQ ID No. 5 or SEQ ID No. 7, where values such as at least 85%, at least 85%, at least 87%, at least 88%, at least 89%, at least 90%, at least 91%, at least 92%, at least 93%, at least 94%, at least 95%, at least 96%, at least 97%, at least 98%, and at least 99% sequence homology are envisioned. The VP2 subunit may come from any one or more of EHDV-1, EHDV-2 and EHDV-6 serotypes, where the immunogenic composition or vaccine of the present disclosure may include one or more VP2 subunits.

In one aspect, the immunogenic composition or vaccine of the present disclosure comprises a VP5 subunit which is the protein expressed by a sequence having at least 90% sequence homology with SEQ ID No. 2 or SEQ ID No.4 or having an amino acid sequence that has at least 90% sequence homology with SEQ ID No. 6 or SEQ ID No. 8 and a VP2 subunit which is the protein expressed by a sequence having at least 90% sequence homology with SEQ ID No. 1 or SEQ ID No. 3 or having an amino acid sequence that has at least 90% sequence homology with SEQ ID No. 5 or SEQ ID No. 7.

In another aspect, the immunogenic composition or vaccine of the present disclosure comprises two or more VP5 subunits expressed by a sequence having at least 90% sequence homology with SEQ ID No. 2 or SEQ ID No.4 or having an amino acid sequence that has at least 90% sequence homology with SEQ ID No. 6 or SEQ ID No. 8.

In a further aspect, the immunogenic composition or vaccine of the present disclosure comprises two or more VP2 subunits which are expressed by a sequence having at least 90% sequence homology with SEQ ID No. 1 or SEQ ID No. 3 or having an amino acid sequence that has at least 90% sequence homology with SEQ ID No. 5 or SEQ ID No. 7.

In a further aspect, the immunogenic composition or vaccine of the present disclosure comprises a VP2 subunit. In a preferred aspect, the VP2 subunit is from an EHDV-2 or EHDV-6. In another aspect, the immunogenic composition of the present disclosure comprises a VP2 and VP5 subunit. In a preferred aspect, the VP2 subunit is from an EHDV-2 or EHDV-6, or both. In yet another aspect, the immunogenic composition or vaccine of the present disclosure comprises a VP5 subunit. In a preferred aspect, the VP5 subunit is from an EHDV-2 or EHDV-6, or both.

In another aspect, the disclosure provides immunogenic compositions or vaccines comprising a vector or plasmid and an acceptable pharmaceutical or veterinary vehicle, the vector or plasmid comprising a nucleotide sequence of the genome of EHDV, a subunit, a homologue, or fragment thereof. In one aspect, the immunogenic composition or vaccine further comprises a gene coding for an expression product capable of inhibiting or retarding the establishment or development of a virus. Preferred nucleotide sequences have at least 90%, at least 91%, at least 92%, at least 93%, at least 94%, at least 95%, at least 96%, at least 97%, at least 98%, or at least 99% sequence homology with a sequence selected from the group consisting of SEQ ID Nos. 1-4, and combinations thereof.

The present disclosure also relates to immunogenic compositions or vaccines comprising a cell and an acceptable pharmaceutical or veterinary vehicle, wherein the cell is transformed with a nucleotide sequence of the genome of EDHV, a subunit, a homologue, or a fragment thereof. Preferred nucleotide sequences have at least 90%, at least 91%, at least 92%, at least 93%, at least 94%, at least 95%, at least 96%, at least 97%, at least 98%, or at least 99% sequence homology with a sequence selected from the group consisting of SEQ ID Nos. 1-4, and combinations thereof.

In one aspect, the present disclosure provides for a vector having the sequence for one or more of a VP2 or VP5 subunit, where the vector expresses the proteins for the subunits in the recipient. Possible combinations, include, but are not limited to, a vector with two or more VP2 sequences, a vector with two or more VP5 sequences, or a vector with one or more VP2 sequences and one or more VP5 sequences, where the VP2 and/or VP5 subunits may come from any one or more of EHDV-1, EHDV-2 and EHDV-6.

In a further aspect, the immunogenic composition or vaccine may comprise nucleic acid. The nucleic acid component may be inactivated, modified live, or attenuated. In preferred forms, the nucleic acid has at least 95%, at least 96%, at least 97%, at least 98%, or at least 99% sequence homology with at least one of the nucleotide sequences selected from SEQ ID No. 1, SEQ ID No. 2, SEQ ID No. 3, and SEQ ID No. 4. In another aspect, the nucleic acid sequence encodes an amino acid sequence that has at least 95%, at least 96%, at least 97%, at least 98%, or at least 99% sequence homology with at least one of the amino acid sequences selected from SEQ ID No. 5, SEQ ID No. 6, SEQ ID No. 7, and SEQ ID No. 8.

In one aspect, the immunogenic composition may also comprise additional elements selected from the group consisting of antigens, pharmaceutical carriers, adjuvants, preservatives, stabilizers, or combinations thereof. These additional elements can be combined with any of the protein or nucleic acid immunogenic compositions or vaccines described herein.

Pharmaceutically acceptable vehicle or carrier is understood as designating a compound or a combination of compounds entering into a pharmaceutical composition or vaccine which does not provoke secondary reactions and which allows, for example, the facilitation of the administration of the active compound, an increase in its duration of life and/or its efficacy in the body, an increase in its solubility in solution or alternatively an improvement in its conservation. These pharmaceutically acceptable vehicles are well known and will be adapted by the person skilled in the art as a function of the nature and of the mode of administration of the chosen active compound.

As far as the vaccine formulations are concerned, these can comprise adjuvants of the appropriate immunity which are known to the person skilled in the art, such as, for example, Montanide ISA 25, aluminum hydroxide, a representative of the family of muramyl peptides such as one of the peptide derivatives of N-acetyl muramyl, a bacterial lysate, carbomers, or alternatively Freund's incomplete adjuvant. In a preferred aspect, the adjuvant is Montanide ISA 25.

The immunogenic composition and vaccine described herein can be administered by the systemic route, in particular by the intravenous route, by the intramuscular, intradermal or subcutaneous route, or by the oral or nasal, or intranasal route. In a more preferred manner, the immunogenic composition or vaccine composition according to the disclosure will be administered by the intramuscular route, through the food, or by nebulization several times, staggered over time. In a further preferred aspect, the immunogenic composition or vaccine composition according to the disclosure will be administered subcutaneously. In preferred forms, such subcutaneous administration occurs twice with a three-week interval.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective against EHD.

The administration of the immunogenic composition or vaccine according to the present disclosure may be administered one time, two times, three times, four times, five times, six times, seven times, eight times, nine times, or at least 10 times. In one aspect, the immunogenic composition or vaccine of the present disclosure is effective after a single dose administration.

For example, the immunogenic composition or vaccine according to the present disclosure may be administered one time or several times, spread out over time in an amount of about 0.1 to 1000 µg per kilogram weight of the animal, where values and ranges such as, but not limited to, 0.5 to 800 µg per kilogram weight of the animal, 1 to 1000 µg per kilogram weight of the animal, 1 to 500 µg per kilogram weight of the animal, 1 to 300 µg per kilogram weight of the animal, 1 to 200 µg per kilogram weight of the animal, 1 to 150 µg per kilogram weight of the animal, 1 to 125 µg per kilogram weight of the animal, 1 to 100 µg per kilogram weight of the animal, 5 µg per kilogram weight of the animal, 10 µg per kilogram weight of the animal, 15 µg per kilogram weight of the animal, 20 µg per kilogram weight of the animal, 25 µg per kilogram weight of the animal, 30 µg per kilogram weight of the animal, 35 µg per kilogram weight of the animal, 40 µg per kilogram weight of the animal, 45 µg per kilogram weight of the animal, 50 µg per kilogram weight of the animal, 55 µg per kilogram weight of the animal, 60 µg per kilogram weight of the animal, 65 µg per kilogram weight of the animal, 70 µg per kilogram weight of the animal, 75 µg per kilogram weight of the animal, 80 µg per kilogram weight of the animal, 85 µg per kilogram weight of the animal, 90 µg per kilogram weight of the animal, 95 µg per kilogram weight of the animal, 100 µg per kilogram weight of the animal, 125 µg per kilogram weight of the animal, 150 µg per kilogram weight of the animal, 200 µg per kilogram weight of the animal, 250 µg per kilogram weight of the animal, 300 µg per kilogram weight of the animal, 400 µg per kilogram weight of the animal, 500 µg per kilogram weight of the animal, 600 µg per kilogram weight of the animal, 700 µg per kilogram weight of the animal, 800 µg per kilogram weight of the animal, 900 µg per kilogram weight of the animal and 1000 µg per kilogram weight of the animal are envisioned.

In some preferred forms, the above amounts are also provided without reference to the weight of the animal.

In some preferred forms where more than one dose or administration is provided, the time between administrations is from 1 day to 12 weeks, more preferably between 3 days and 11 weeks, still more preferably between 5 days and 10 weeks, even more preferably between 1 week and 9 weeks, still more preferably between 9 days and 8 weeks, even more preferably between 11 days and 7 weeks, still more preferably between 13 days and 6 weeks, even more preferably between 15 days and 5 weeks, still more preferably between 17 days and 4 weeks, and still more preferably about 3 weeks.

According to the present disclosure, the immunogenic composition or vaccine may include an antigen from at least one further pathogen other than EHDV, including, but not limited to the pathogens responsible for Bluetongue (BT), African Horse Sickness, Crimean-Congo hemorrhagic fever, Foot and mouth disease, lumpy skin disease, peste des petit ruminants, rinderpest virus, schmallenberg virus, sheep pox, goat pox, West Nile virus, BVD, calf diphtheria, calf pneumonia, fog fever, IBR, TB, thrombosis, trypanosomosis, and combinations thereof. Further, the at least one further pathogen may be selected from, but is not limited to, *Burcella* spp., *cryptosporidium, Dermatophilus congolensis, Escherichia coli, Leptospira interrogans, Listeria monocytogenes*, pseudocowpox, *Coxiella burneti*, rabies, Trichopyton, Microspora, *Salmonella* spp., *Mycobacterium bovis, Mycoplasma Bovis* and combinations thereof.

A method for reducing the incidence or severity of clinical symptoms of EHD is provided, where the steps of the method include administration of the immunogenic composition or vaccine against EHD to a subject in need thereof.

The clinical symptoms reduced in incidence or severity include, but are not limited to, loss of appetite, loss of fear of people, weakness, excessive salivation, rapid pulse, rapid respiration rate, fever, lying in bodies of water to reduce body temperature, unconsciousness, blue tongue, head swelling, neck swelling, sloughing or breaking of hooves, lameness, shock, hemorrhages in tissues, including skin and gastrointestinal tract, death, and combinations thereof.

In one aspect, the method of the present invention reduces the clinical symptoms and/or the severity or incidence of clinical symptoms of EHD in a subject by at least 10%, at least 20%, at least 30%, at least 40%, at least 50%, at least 60%, at least 70%, at least 80%, at least 90%, at least 95%, from about 10% to 50%, from about 10% to 90%, from about 30% to 50%, from about 20% to 60%, from about 30% to 80%, from about 30% to 50%, and from about 50% to 95%, with all values within the recited ranges being envisioned. The reduction of clinical symptoms and/or the reduction of the incidence or severity of clinical symptoms is when compared to a subject not administered the immunogenic composition or vaccine of the present disclosure.

A method for preventing clinical symptoms or reducing the incidence or severity of symptoms of subclinical infection of EHDV is provided, where the steps of the method include administration of the immunogenic composition or vaccine against EHD to a subject in need thereof.

Subclinical infection presents with viremia, virus shedding and mild symptoms included, but not limited to, mild fever and/or loss of appetite. Clinical symptom includes subclinical with more severe fever, oral ulcers, excessive salivation, lameness, coronitis, and combinations thereof.

In one aspect, the method of the present invention reduces the symptoms of subclinical EHDV infection and/or the severity or incidence of the symptoms of subclinical EHDV infection in a subject by at least 10%, at least 20%, at least 30%, at least 40%, at least 50%, at least 60%, at least 70%, at least 80%, at least 90%, at least 95%, from about 10% to 50%, from about 10% to 90%, from about 30% to 50%, from about 20% to 60%, from about 30% to 80%, from about 30% to 50%, and from about 50% to 95%, with all values within the recited ranges being envisioned. The reduction of clinical symptoms and/or the reduction of the incidence or severity of clinical symptoms is when compared to a subject not administered the immunogenic composition or vaccine of the present disclosure.

A method for reducing EHD viremia is provided, where the steps of the method include administration of the immunogenic composition or vaccine against EHD to a subject in need thereof.

The EHD viremia is preferably reduced by at least 10%, at least 20%, at least 30%, at least 40%, at least 50%, at least 60%, at least 70%, at least 80%, at least 90%, or at least 95%, when compared to an animal not receiving the immunogenic composition or vaccine of the present disclosure.

The immunogenic composition or vaccine provided in this disclosure may be administered to any subject in need thereof. In one aspect, the subject is selected from, but not limited to, cattle, goats, sheep, giraffes, yaks, deer, antelope, macropods, or any other animal considered a ruminant.

It must be understood that the present disclosure does not relate to the genomic nucleotide sequences taken in their natural environment, that is to say, in the natural state. It concerns sequences for which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the disclosure to be carried by vectors.

DEFINITIONS

"Homologous nucleotide sequence" or "having sequence homology" in the sense of the present disclosure is understood as meaning a nucleotide or amino acid sequence having at least a percentage identity with the nucleotide bases of a or amino acid sequence according to the disclosure of at least 80%, where ranges and values, including but not limited to, from 80% to 85%, 85% to 96%, 80% or 95%, 80%, 81%, 82%, 83%, 84%, 85%, 86%, 87%, 88%, 89%, 90%, 91%, 92%, 93%, 94%, 95%, 95.5%, 96%, 96.5%, 97%, 97.5%, 98%, 98.5%, 99%, 99.5%, 99.9%, and higher are envisioned for the present disclosure, where this percentage being purely statistical and it being possible to distribute the differences between the two sequences at random and over the whole of their length.

An "immunogenic composition" as used herein, means a EHDV composition which elicits an "immunological response" in the host of a cellular and/or antibody-mediated immune response to the EHDV sequence, whether the sequence is killed/inactivated, modified live, a subunit of the nucleotide sequence or peptide expressed by that sequence, or in a vector. Preferably, this immunogenic composition is capable of reducing the incidence or severity of clinical and subclinical signs of infection and/or conferring protective immunity against EHDV infection or subclinical infection and the clinical symptoms associated therewith.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well-defined and only one value for the sequence identity between two compared sequences which value corresponds to the value obtained for the best or optimal alignment.

The BLAST N or BLAST P "BLAST 2 sequence", software which is available in html at the web site ncbi.nlm-.nih.gov/gorf/b12, is habitually used by the skilled man for comparing and determining the identity between two sequences and calculates the statistical significance.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated or purified" means altered "by the hand of man" from its natural state, i.e., if it occurs in nature, it has been changed or removed from its original environment, or both. For example, a polynucleotide or polypeptide naturally present in a living organism is not "isolated or purified," but the same polynucleotide or polypeptide separated from the coexisting materials of its natural state is "isolated or purified", as the term is employed herein.

"Modified or modified live" nucleotide sequence will be understood as meaning any nucleotide sequence obtained by mutagenesis according to techniques well known to the person skilled in the art, and containing modifications with respect to the normal sequences according to the disclosure, for example mutations in the regulatory and/or promoter sequences of polypeptide expression, especially leading to a modification of the rate of expression of said polypeptide or to a modulation of the replicative cycle.

"Nucleotide, polynucleotide, nucleic acid or nucleic acid sequence" will be understood according to the present disclosure as meaning both a double-stranded or single-stranded RNA or DNA in the monomeric and dimeric (so-called in tandem) forms and the transcription products of said DNAs.

All ranges provided herein include each and every value in the range as well as all sub-ranges there-in-between as if each such value or sub-range was disclosed. Further, all aspects and embodiments of the disclosure comprise, consist essentially of, or consist of any aspect or embodiment, or combination of aspects and embodiments disclosed herein.

EXAMPLES

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Example 1

This example illustrates the efficacy of the immunogenic composition or vaccine of the present disclosure.

Figures 1, 2:
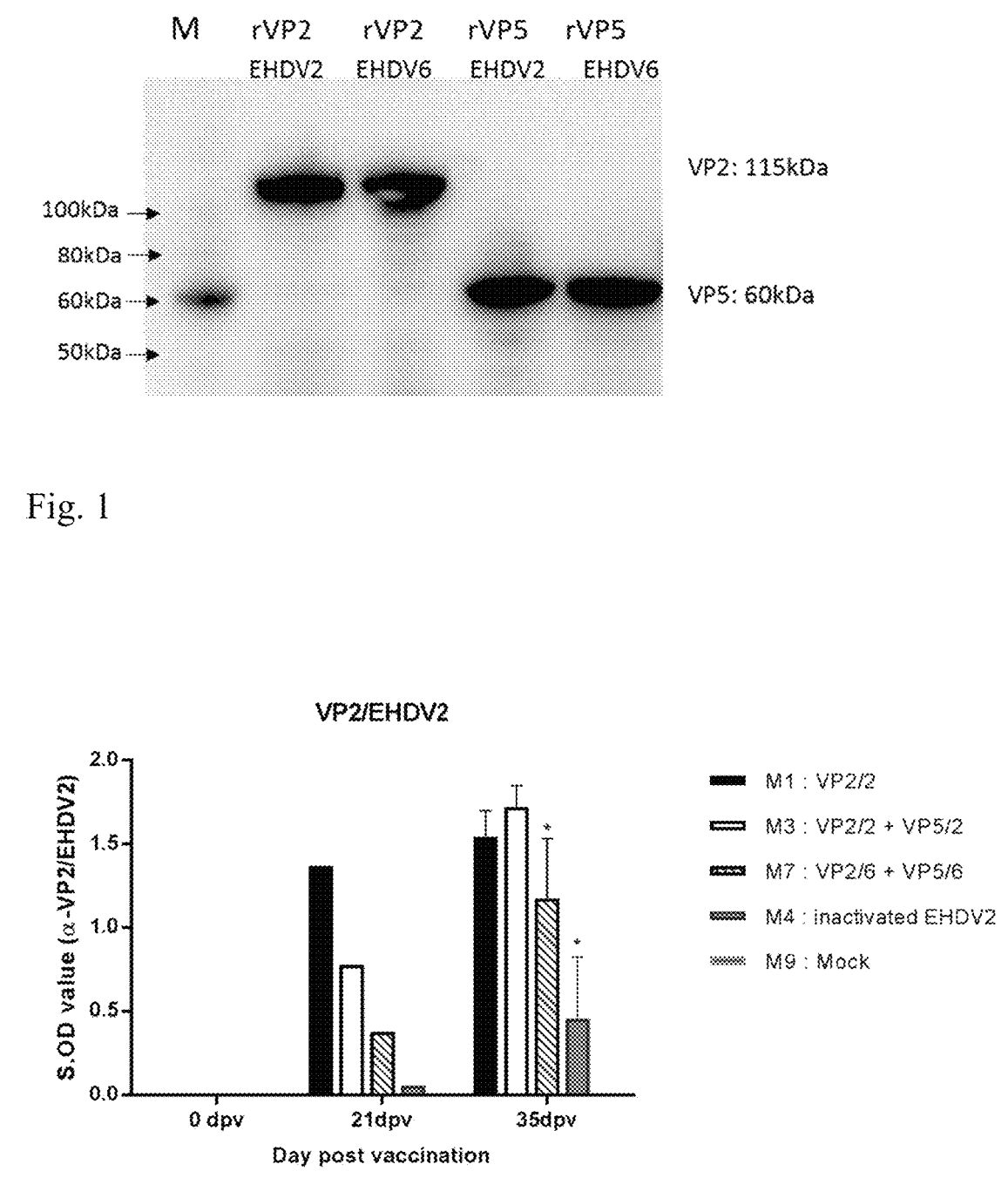

The expression of VP2 and VP5 proteins of EHDV in baculovirus. The recombinant VP2 and VP5 proteins of EHDV2 and EHDV6 were produced using the baculovirus expression system (BaculoDirect vector, Invitrogen, US). The expression of each VP2 and VP5 protein was confirmed by western blot using anti-histidine tag antibodies and polyclonal serum against EHDV2. The expressed proteins revealed a band of 60 kDa and VP5 and 115 kDa for VP2 (FIG. 1).

Immunogenicity Studies of Recombinant EHDV Vaccines in Mice.

1) Experimental Groups

Nine groups of mice with 5 animals per group were immunized with either VP2 or VP5 or combination of VP2 & VP5 proteins of EHDV2 or EHDV6. EHDV2 and EHDV 6 inactivated virus vaccines were used as a positive control for each serotype, as detailed in Table 1. Vaccines (10-20 µg of purified protein mixed with adjuvant Montanide ISA25, Seppic, in 200 ul) were administered subcutaneously twice at an interval of 3 weeks. Mice were bled via saphenous vein on 0 and 21 day post vaccination (dpv) and at the end of study on 35 dpv.

TABLE 1

Experimental groups of mouse study #1

| Group | Vaccine candidate | Doses |
|---|---|---|
| M1 | rVP2/EHDV 2 (VP2/2) | 200 µl (20 ug purified protein) |
| M2 | rVP5/EHDV 2 (VP5/2) | (with adjuvant; ISA25) |
| M3 | rVP2/EHDV2 + rVP5/EHDV 2 | |
| M4 | EHDV 2 inactivated virus | $10^5$ TCID$_{50}$ with adjuvant |
| M5 | rVP2/EHDV 6 (VP2/6) | 200 µl (20 ug purified protein) |
| M6 | rVP5/EHDV 6 (VP5/6) | (with adjuvant; ISA25) |
| M7 | rVP2/EHDV6 + rVP5/EHDV 6 | |
| M8 | EHDV 6 inactivated virus | $10^5$ TCID$_{50}$ with adjuvant |
| M9 | Mock | 200 µl of PBS with adjuvant |

Evaluation of Immunogenicity (Vaccine Efficacy)

ELISA Test

ELISA test was used to evaluate the humoral immune responses in serum from immunized mice. Pooled serum samples collected on 0 and 21 dpv and individual serum samples collected on 35 dpv were tested. Briefly, Maxisorp 96-well plates were coated with respective recombinant protein (100 ng/well). The negative control wells were coated with baculovirus-infected insect cell lysate. Serum samples were diluted 1/100 and allowed to react with respective antigens in 96 well plate for 1 hour at room temperature. Anti-mouse IgG conjugated with HRP was used as secondary antibody. Then plates were incubated with TMB substrate for 15 minutes and after addition of the stop solution (0.16 M sulfuric acid) OD values were measured in the plate reader at 450 nm.

Protein specific signal was calculated as shown: Specific OD value=(OD of sample−OD of negative serum) in target protein coated well−(OD of sample−OD of negative serum) in proteins from baculovirus infected cell lysate−coated well Mice immunized with different recombinant proteins elicited EHDV-specific antibodies against target proteins as shown in FIGS. 2, 3, 4 and 5. Individual data of ELISA testing of samples are shown in Tables 2 and 3.

TABLE 2

Specific OD value of each recombinant protein in ELISA test.
Specific OD value of recombinant protein

| | α-VP2-EHDV2 | | | | | α-VP5-EHDV2 | | | | |
|---|---|---|---|---|---|---|---|---|---|---|
| DPV† | M1 VP2/2 | M3 VP2/2 + VP5/2 | M7 VP2/6 + VP5/6 | M4 Inact. EHDV2 | M9 Mock | M2 VP5/2 | M3 VP2/2 + VP5/2 | M7 VP2/6 + VP5/6 | M4 Inact. EHDV2 | M9 Mock |
| 0 D | −0.048 | 0.013 | 0.005 | 0.076 | 0 | −0.038 | 0.055 | 0.028 | 0.057 | 0 |
| 21 D | 1.370 | 0.776 | 0.378 | 0.058 | 0 | 0.328 | 0.683 | 0.551 | 0.029 | 0 |
| 35 D | 1.542 | 1.720 | 1.176 | 0.458 | 0 | 0.932 | 1.466 | 1.438 | 0.441 | 0 |
| 35 D SD* | 0.158 | 0.129 | 0.357 | 0.365 | 0 | 0.470 | 0.267 | 0.244 | 0.428 | 0 |

TABLE 2-continued

Specific OD value of each recombinant protein in ELISA test.
Specific OD value of recombinant protein

| | α-VP2-EHDV6 | | | | | α-VP5-EHDV6 | | | | |
|---|---|---|---|---|---|---|---|---|---|---|
| DPV | M5 VP2/6 | M7 VP2/6 + VP5/6 | M3 VP2/2 + VP5/2 | M8 Inact. EHDV6 | M9 Mock | M6 VP5/6 | M7 VP2/6 + VP5/6 | M3 VP2/2 + VP5/2 | M8 Inact. EHDV6 | M9 Mock |
| 0 D | 0.009 | −0.182 | −0.086 | 0.006 | 0 | −0.001 | 0.002 | −0.025 | 0.030 | 0 |
| 21 D | 2.204 | 2.124 | 0.094 | 0.017 | 0 | 0.083 | 0.233 | 0.294 | 0.068 | 0 |
| 35 D | 2.577 | 2.432 | 0.516 | 0.269 | 0 | 0.892 | 0.904 | 0.759 | 0.244 | 0 |
| 35 D SD | 0.05 | 0.102 | 0.213 | 0.131 | 0 | 0.230 | 0.170 | 0.163 | 0.069 | 0 |

DPV[†] = day post vaccination; SD* = standard deviation.

TABLE 3

The specific OD values of serum from individual animals at 35 dpv

Specific OD. value of serum from immunized mouse against respective protein

| Group | mouse # | Anti-VP2/ EHDV2 | Anti-VP5/ EHDV2 | Anti-VP2/ EHDV6 | Anti-VP5/ EHDV6 |
|---|---|---|---|---|---|
| M1: VP2/2 | 1-1 | 1.675 | NT* | NT | NT |
| | 1-2 | 1.443 | NT | NT | NT |
| | 1-3 | 1.313 | NT | NT | NT |
| | 1-4 | 1.624 | NT | NT | NT |
| | 1-5 | 1.656 | NT | NT | NT |
| M2: VP5/2 | 2-1 | NT | 1.370 | NT | NT |
| | 2-2 | NT | 1.404 | NT | NT |
| | 2-3 | NT | 0.876 | NT | NT |
| | 2-4 | NT | 0.751 | NT | NT |
| | 2-5 | NT | 0.861 | NT | NT |
| M3: VP2/2 + VP5/2 | 3-1 | 1.599 | 1.367 | 0.482 | 0.727 |
| | 3-2 | 1.737 | 1.571 | 0.697 | 0.820 |
| | 3-3 | 1.599 | 1.084 | 0.217 | 0.496 |
| | 3-4 | 1.911 | 1.807 | 0.745 | 0.920 |
| | 3-5 | 1.755 | 1.501 | 0.438 | 0.834 |
| M4: Inactivated EHDV2 | 4-1 | 0.022 | 0.557 | NT | NT |
| | 4-2 | 0.535 | 0.517 | NT | NT |
| | 4-3 | 0.735 | 0.736 | NT | NT |
| | 4-4 | 0.859 | 0.948 | NT | NT |
| | 4-5 | 0.141 | 0.026 | NT | NT |
| M5: VP2/6 | 5-1 | NT | NT | 2.508 | NT |
| | 5-2 | NT | NT | 2.556 | NT |
| | 5-3 | NT | NT | 2.621 | NT |
| | 5-4 | NT | NT | 2.622 | NT |
| | 5-5 | NT | NT | | NT |
| M6: VP5/6 | 6-1 | NT | NT | NT | 0.781 |
| | 6-2 | NT | NT | NT | 1.135 |
| | 6-3 | NT | NT | NT | 0.907 |
| | 6-4 | NT | NT | NT | 1.073 |
| | 6-5 | NT | NT | NT | 0.565 |
| M7: VP2/6 + VP5/6 | 7-1 | 1.599 | 1.695 | 2.525 | 1.064 |
| | 7-2 | 0.868 | 1.382 | 2.426 | 0.942 |
| | 7-3 | 1.529 | 1.666 | 2.370 | 1.018 |
| | 7-4 | 0.981 | 1.111 | 2.299 | 0.631 |
| | 7-5 | 0.904 | 1.337 | 2.539 | 0.868 |
| M8: Inactivated EHDV 6 | 8-1 | NT | NT | 0.117 | 0.283 |
| | 8-2 | NT | NT | 0.325 | 0.254 |
| | 8-3 | NT | NT | 0.374 | 0.318 |
| | 8-4 | NT | NT | 0.390 | 0.231 |
| | 8-5 | NT | NT | 0.242 | 0.136 |
| M9: Mock | 9-1 | 0 | 0 | 0 | 0 |
| | 9-2 | 0 | 0 | 0 | 0 |
| | 9-3 | 0 | 0 | 0 | 0 |
| | 9-4 | 0 | 0 | 0 | 0 |
| | 9-5 | 0 | 0 | 0 | 0 |

Figure 4:
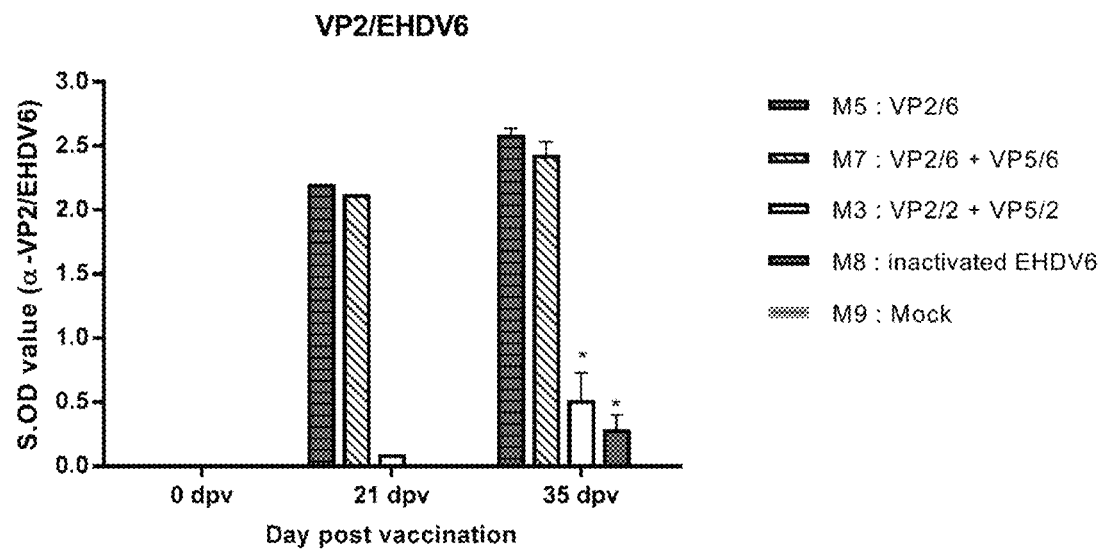
FIG. 4 is a graph illustrating specific OD values of serum from immunized mice against VP2/EHDV 6 proteins (*=$p<0.05$)
Figure 5:
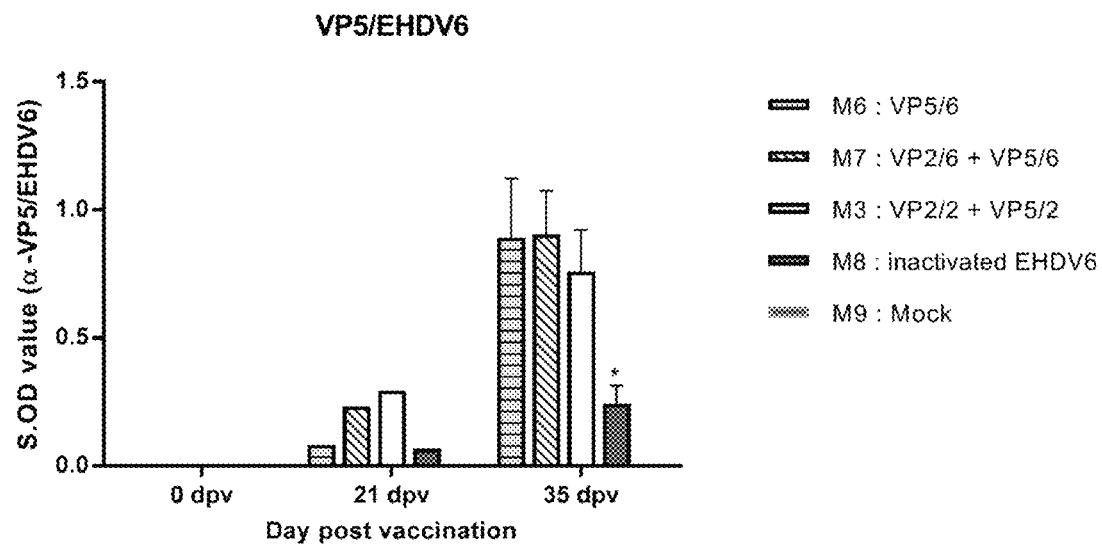
FIG. 5 is a graph illustrating specific OD values of serum from immunized mice against VP5/EHDV6 protein (*=$p<0.05$)

There was a strong seroconversion against homologous protein in vaccinates of all recombinant vaccine administered groups detected as early as 21 dpv after single immunization. ELISA signal was increased on 35 dpv after booster vaccination. In addition, sera from mice immunized with VP2+VP5 of EHDV2 (Group M3) revealed specific OD signal against VP2 of EHDV 6 and VP5 of EHDV6 (FIGS. 2 and 3). Sera from mice immunized with VP2+VP5 of EHDV6 (Group M7) also showed cross reactivity against VP2 of EHDV2 and VP5 of EHDV2 (FIGS. 4 and 5). This indicates serological cross-reactivity between the VP2 and VP5 proteins of EHDV2 and EHDV6.

Virus Neutralization Test (VN Test)

The virus neutralization test was done based on OIE and USDA protocols. EHDV serotype 2 (strain 600544 or EHDV2/Alberta Strain) and EHDV serotype 6 (2006 US isolate were C/cervidae/Ohio/12-3437-8/2012) used for neutralization test. In brief, sera from immunized mice were initially diluted 10 fold and then 2 fold dilutions from 1/10 to 1/3200 were made in 96-well culture plate. Virus with 100 $TCID_{50}/50$ ul was added into each well and the plates were incubated for 1 hour at 37° C. Then Vero cells were added ($2 \times 10^4$ cell per well) and incubated for 5 days at 37° C. with 5% $CO_2$. Wells were scored for the degree of CPE. The serum titer was calculated and recorded as the highest serum dilution capable of preventing virus replication (CPE) in more than 50% of the infected wells.

Figure 6:
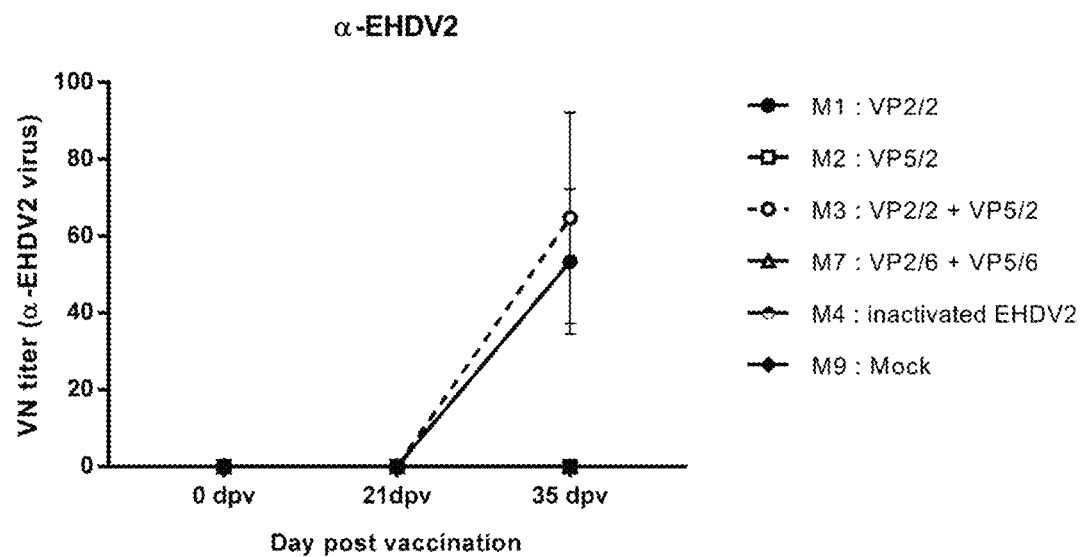
FIG. 6 is a graph illustrating Virus Neutralization titers of sera from immunized mice against EHDV 2 virus.
Figures 7, 8:
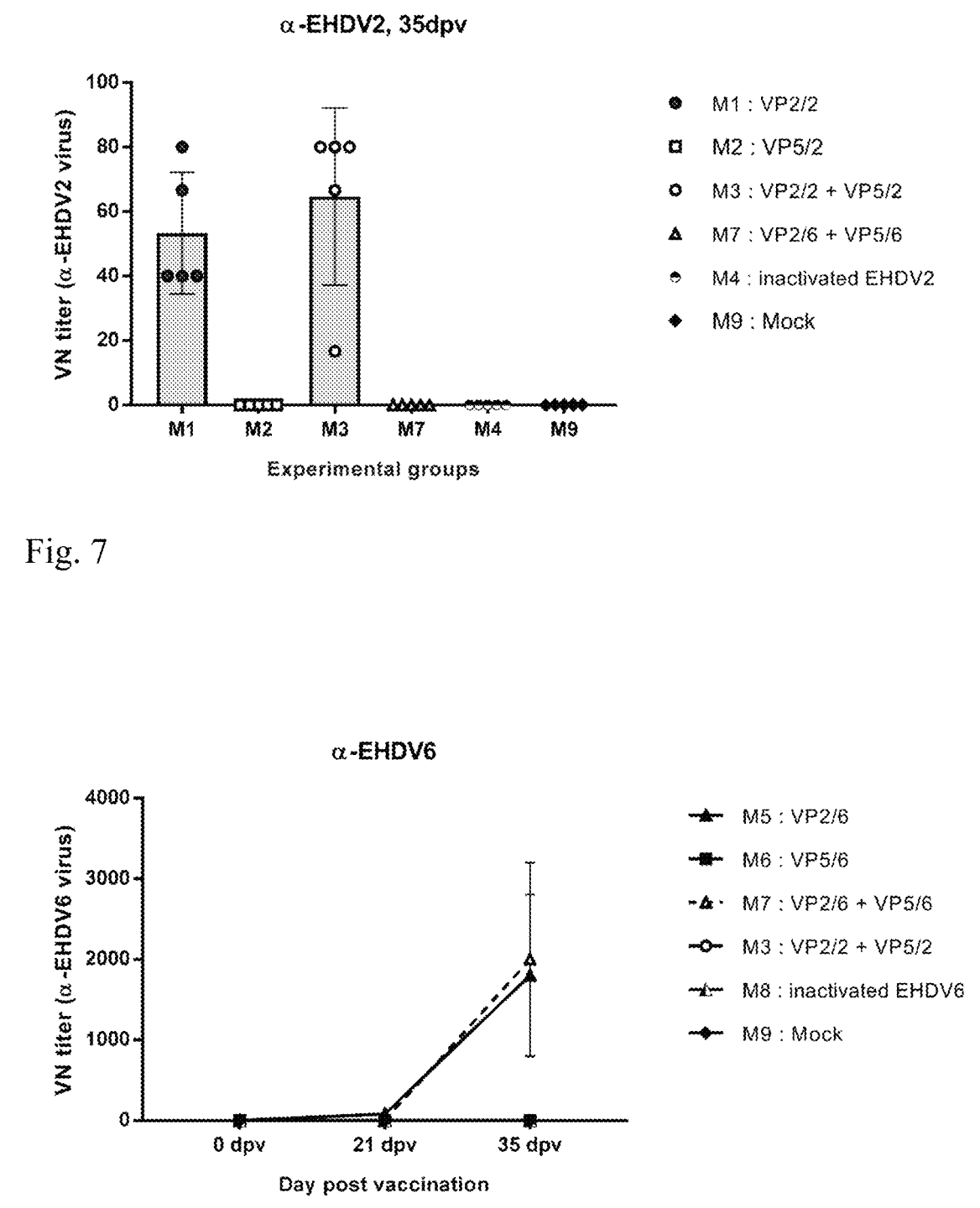

Virus neutralization assays against EHDV2 showed neutralizing activity in serum from mice immunized with VP2 of EHDV2 (Group M1) and with combination of VP2 and VP5 proteins of EHDV2 (Group M3) on 35 dpv. Sera from mice, immunized with VP5 alone (Group M2), with combination of VP2+VP5 of EHDV6 (Group M7) and inactivated EHDV2 virus (Group M4) did not show any anti-EHDV2 neutralizing activity (FIGS. 6 & 7, Table 4, 5). No significant neutralizing titers were detected on 21 dpv after single immunization. In contrast to ELISA results, there was no cross-neutralizing activity between EHDV2 and EHDV6 serotypes.

TABLE 4

VN titer of serum against EHDV serotype 2 virus

VN titer (mean) against EHDV serotype 2 virus

| DPV | M1 VP2/2 | M2 VP5/2 | M3 VP2/2 + VP5/2 | M7 VP2/6 + VP5/6 | M4 I-EHDV2 | M9 Mock |
|---|---|---|---|---|---|---|
| 0 D | 0 | 0 | 0 | 0 | 0 | 0 |
| 21 D | 0 | 0 | 0 | 0 | 0 | 0 |
| 35 D (Mean ± SD) | 53.33 ± 19.3 | 0 | 64.6 ± 27 | 0 | 0 | 0 |

TABLE 5

VN titer of serum from each individual mouse at 35 dpv

VN titer of individual serum sample against EHDV2 virus

| | #1 | #2 | #3 | #4 | #5 |
|---|---|---|---|---|---|
| M1: VP2/2 | 40 | 66.67 | 40 | 40 | 80 |
| M2: VP5/2 | 0 | 0 | 0 | 0 | 0 |
| M3: VP2/2 + VP5/2 | 80 | 66.67 | 80 | 80 | 16.67 |
| M7: VP2/6 + VP5/6 | 0 | 0 | 0 | 0 | 0 |
| M4: I-EHDV2 | 0 | 0 | 0 | 0 | 0 |
| M9: Mock | 0 | 0 | 0 | 0 | 0 |

Figures 9, 10:
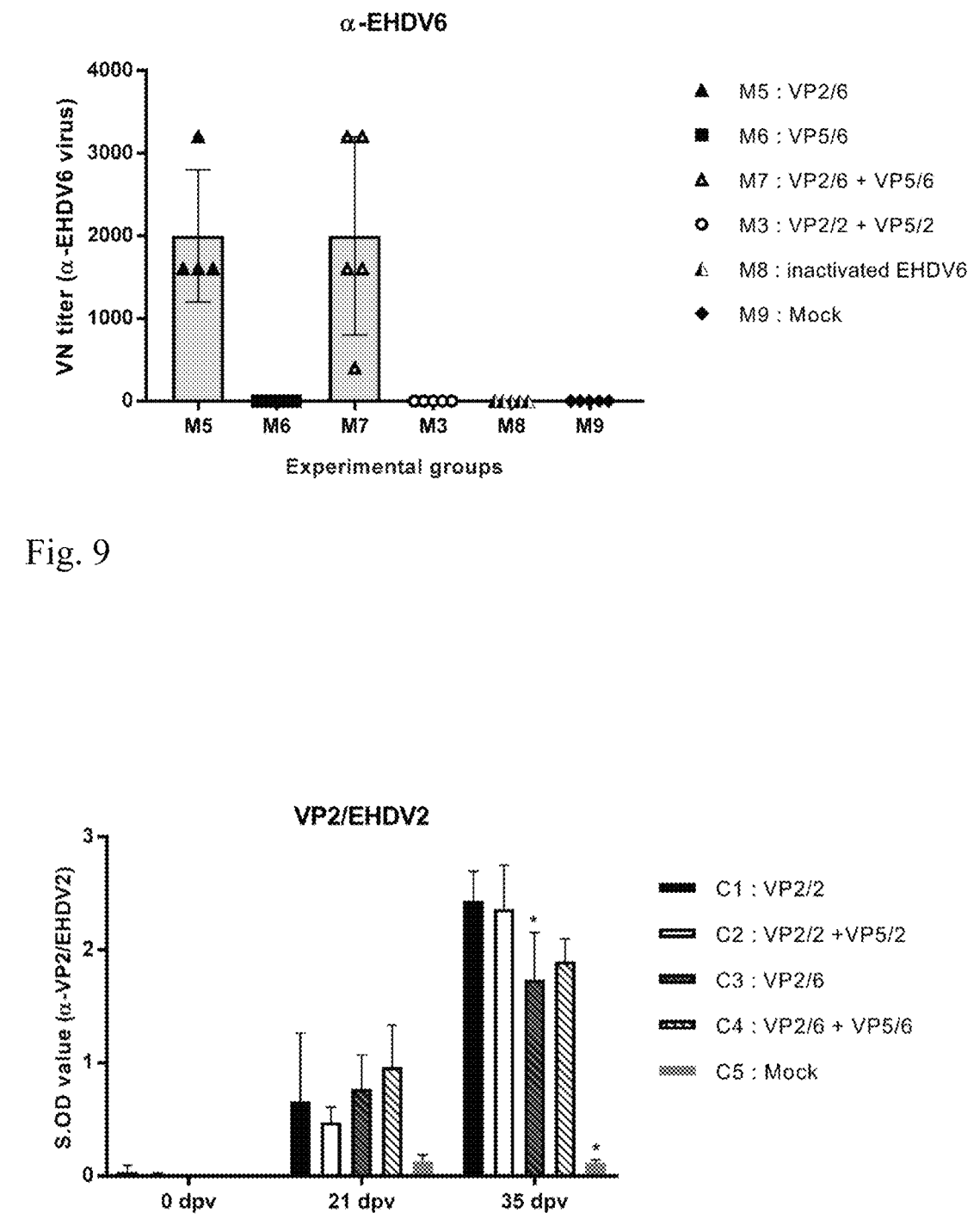

Virus neutralization assays against EHDV6 showed neutralizing activity in serum from mice immunized with VP2 of EHDV6 (Group M5) and with a combination of VP2 and VP5 proteins of EHDV6 (Group M7) at 35 dpv. Some virus neutralizing activity in serum from mice immunized with VP2 of EHDV6 (Group M5) was already observed on day 21 post vaccination. Sera from mice, immunized with VP5 of EHDV6 (Group M6), with combination of VP2+VP5 of EHDV2 (M3) and inactivated EHDV6 virus (M8) did not show any anti-EHDV6 virus neutralizing activity (FIGS. 8 & 9, Table 6, 7). Similarly to the EHDV2 VN assay, there was no cross-neutralizing activity between EHDV2 and EHDV6 serotypes.

TABLE 6

VN titer of serum against EHDV serotype 6 virus

VN titer against EHDV serotype 6 virus

| DPV | M5 VP2/6 | M6 VP5/6 | M7 VP2/6 + VP5/6 | M3 VP2/2 + VP5/2 | M8 I-EHDV6 | M9 Mock |
|---|---|---|---|---|---|---|
| 0 D | 0 | 0 | 0 | 0 | 0 | 0 |
| 21 D | 80 | 0 | 0 | 0 | 0 | 0 |
| 35 D (Mean ± SD) | 1800 ± 1006 | 0 | 2000 ± 1200 | 0 | 0 | 0 |

TABLE 7

VN titer of serum from individual mouse at 35 dpv

VN titer of individual serum against EHDV2 virus

| | #1 | #2 | #3 | #4 | #5 |
|---|---|---|---|---|---|
| M5: VP2/6 | 1600 | 3200 | 1600 | 800 | |
| M6: VP5/6 | 0 | 0 | 0 | 0 | 0 |
| M7: VP2/6 + VP5/6 | 3200 | 400 | 1600 | 1600 | 3200 |
| M3: VP2/2 + VP5/2 | 0 | 0 | 0 | 0 | 0 |

TABLE 7-continued

VN titer of serum from individual mouse at 35 dpv

VN titer of individual serum against EHDV2 virus

| | #1 | #2 | #3 | #4 | #5 |
|---|---|---|---|---|---|
| M8: I-EHDV6 | 0 | 0 | 0 | 0 | 0 |
| M9: Mock | 0 | 0 | 0 | 0 | 0 |

Immunogenicity Studies of Recombinant EHDV Vaccines in Cattle

Experimental Groups

Five groups of cattle with 3 animals per group were immunized with either VP2 or a combination of VP2 & VP5 proteins of EHDV2 or EHDV6. PBS with adjuvant was used for mock-control, as detailed in Table 8. The purified protein (150 µg) mixed with Montanide ISA25 adjuvant (Seppic, France) in 2 mL per dose, was administered subcutaneously twice at an interval of 3 weeks. Blood was collected via the jugular vein on days 0, 21 and 35 post vaccination (dpv). The collected blood was centrifuged at 2,000 rpm for 10 minutes to collect the serum. Serum samples for VN test were mixed with equal volume of PBS and incubated at 56° C. for 30 minutes to inactive the complement. All serum samples were stored at −70° C. until use.

TABLE 8

The experimental groups of cattle study

| Group | Vaccine candidate | Dose | Animals |
|---|---|---|---|
| C1 | rVP2/EHDV 2 | 2 ml | 3 |
| C2 | rVP2/EHDV 2 + rVP5/EHDV 2 | (150 µg purified protein with ISA25) | 3 |
| C3 | rVP2-EHDV 6 | | 3 |

TABLE 8-continued

The experimental groups of cattle study

| Group | Vaccine candidate | Dose | Animals |
|---|---|---|---|
| C4 | rVP2/EHDV 6 + rVP5-EHDV6 | | 3 |
| C5 | Non vaccine control | 2 ml PBS with ISA25 | 3 |

Evaluation of Immunogenicity (Vaccine Efficacy)

ELISA test. ELISA tests to evaluate the humoral immune responses in sera from immunized cattle were done using individual EHDV recombinant proteins as coating antigens. Briefly, a Maxisorp 96 well plate was coated with respective recombinant protein (100 ng/well). The negative control wells were coated with baculovirus-infected insect cell lysate. Sera from immunized cattle at 1:200 dilution was added into the well and reacted with respective antigens to analyze the level of specific antibodies. Anti-Bovine IgG conjugated with HRP was used as secondary antibody. The plate was then stained with TMB substrate for 15 minutes and following treatment with 0.16M sulfuric acid to stop the reaction. After staining the OD value was measured at 450 nm.

Protein specific titer was calculated as shown below:

Specific OD value (S.OD value)=(OD of sample−OD of negative serum) in target protein coated well−(OD of sample−OD of negative serum) in protein from baculovirus infected cell−coated well Cattle immunized with different recombinant proteins elicited specific antibodies against each of the proteins, as shown in FIGS. 10, 11, 12 and 13. Individual data of ELISA testing of samples are shown in Tables 9 and 10. There was a strong seroconversion against homologous protein in vaccinates of all recombinant vaccine administered groups detected as early as on 21 dpv after single immunization. ELISA signal was increased on 35 dpv after booster vaccination. In addition, sera from cattle immunized with VP2/EHDV2 (Group C1) and combination of VP2/EHDV2+VP5/EHDV2 (Group C2) revealed cross-reactivity against VP2/EHDV6 and VP5/EHDV6. Similarly, sera from cattle administered VP2/EHDV6 (Group C3) and combination of VP2/EHDV6+VP5/EHDV6 (Group C4) had cross reactivity with recombinant proteins of EHDV2. Similar cross-reactivity between EHDV2 and EHDV6 serotypes was observed in the mice study described above.

TABLE 9

Mean of specific OD value of experimental groups against target proteins
Specific OD value of recombinant protein

| | α-VP2-EHDV2 | | | | | α-VP5-EHDV2 | | |
|---|---|---|---|---|---|---|---|---|
| vaccine | C1: VP2/2 | C2: VP2/2 + VP5/2 | C3: VP2/6 | C4: VP2/6 + VP5/6 | C5: Mock | C2: VP2 + VP5/2 | C4: VP2/6 + VP5/6 | Mock |
| 0 D | 0.043 | 0.003 | 0.006 | 0.072 | 0.007 | 0.001 | 0.021 | 0.001 |
| 21 D | 0.660 | 0.475 | 0.768 | 0.965 | 0.128 | 1.015 | 1.372 | 0.004 |
| 35 D (Mean ± SD) | 2.439 ± 0.26 | 2.364 ± 0.39 | 1.736 ± 0.42 | 1.898 ± 0.2 | 0.122 ± 1.05 | 2.172 ± 0.41 | 2.423 ± 0.34 | 0.165 ± 0.02 |

| | α-VP2-EHDV6 | | | | | α-VP5-EHDV6 | | |
|---|---|---|---|---|---|---|---|---|
| vaccine | VP2/2 | VP2/2 + VP5/2 | VP2/6 | VP2/6 + VP5/6 | Mock | VP2+ VP5/2 | VP2/6 + VP5/6 | Mock |
| 0 D | 0.077 | 0.040 | 0.000 | 0.049 | 0.021 | 0.013 | 0.053 | 0.031 |
| 21 D | 1.258 | 1.554 | 1.585 | 1.964 | 0.242 | 0.264 | 0.625 | 0.220 |
| 35 D (Mean ± SD) | 2.095 ± 0.68 | 2.598 ± 0.35 | 2.925 ± 0.31 | 3.185 ± 0.05 | 0.197 ± 0.06 | 2.091 ± 0.14 | 2.440 ± 0.12 | 0.141 ± 0.09 |

TABLE 10

Specific OD values of serum samples from individual animals
Specific OD values of serum from immunized cattle against target recombinant protein

| Group | # cattle | α-VP2/EHDV 2 | | | α-VP5/EHDV 2 | | |
|---|---|---|---|---|---|---|---|
| | | 0 dpv | 21 dpv | 35 dpv | 0 dpv | 21 dpv | 35 dpv |
| C1: VP2/2 | 677 | −0.007 | 0.177 | 2.276 | N | N | N |
| | 709 | 0.104 | 0.458 | 2.305 | N | N | N |
| | 743 | 0.033 | 1.344 | 2.735 | N | N | N |
| C2: VP2/2 + VP5/2 | 712 | +0.025 | 0.552 | 2.124 | 0.001 | 0.750 | 2.104 |
| | 794 | 0.0272 | 0.552 | 2.158 | 0.002 | 0.663 | 1.797 |
| | 800 | 0.007 | 0.321 | 2.810 | 0.001 | 1.632 | 2.614 |
| C3: VP2/6 | 714 | 0.006 | 0.428 | 1.625 | N | N | N |
| | 792 | 0.768 | 0.888 | 2.199 | N | N | N |
| | 855 | 1.736 | 0.987 | 1.384 | N | N | N |
| C4: VP2/6 + VP5/6 | 742 | 0.051 | 1.391 | 2.039 | 0.032 | 2.101 | 2.731 |
| | 745 | −0.011 | 0.75 | 1.986 | −0.030 | 1.108 | 2.479 |
| | 779 | 0.175 | 0.755 | 1.670 | 0.063 | 0.908 | 2.060 |

TABLE 10-continued

Specific OD values of serum samples from individual animals
Specific OD values of serum from immunized cattle against target recombinant protein

| Mock | 707 | 0.008 | 0.191 | 0.147 | 0.001 | 0.164 | 0.152 |
|---|---|---|---|---|---|---|---|
| | 825 | 0.006 | 0.072 | 0.098 | 0.001 | −0.029 | 0.178 |
| | 851 | 0.007 | 0.121 | 0.122 | 0.002 | −0.122 | 0.165 |

| | # | α-VP2/EHDV 6 | | | α-VP5/EHDV 6 | | |
|---|---|---|---|---|---|---|---|
| Group | cattle | 0 dpv | 21 dpv | 35 dpv | 0 dpv | 21 dpv | 35 dpv |
| C1: VP2/2 | 677 | −0.098 | 0.506 | 1.58115 | N | N | N |
| | 709 | 0.153 | 1.044 | 1.83535 | N | N | N |
| | 743 | 0.177 | 2.224 | 2.86745 | N | N | N |
| C2: VP2/2 + VP5/2 | 712 | −0.066 | 1.189 | 2.4633 | −0.003 | 0.510 | 1.980 |
| | 794 | 0.177 | 1.353 | 2.3407 | 0.019 | 0.391 | 2.041 |
| | 800 | 0.009 | 2.121 | 2.9907 | 0.022 | 0.712 | 2.251 |
| C3: VP2/6 | 714 | 0.032 | 1.062 | 2.812 | N | N | N |
| | 792 | 0.003 | 1.726 | 3.280 | N | N | N |
| | 855 | −0.024 | 1.967 | 2.682 | N | N | N |
| C4: VP2/6 + VP5/6 | 742 | 0.119 | 2.387 | 3.215 | 0.068 | 0.763 | 2.379 |
| | 745 | −0.021 | 1.633 | 3.210 | −0.034 | 0.415 | 2.368 |
| | 779 | 0.968 | 1.872 | 3.129 | 0.126 | 0.698 | 2.574 |
| Mock | 707 | 0.085 | 0.267 | 0.236 | 0.068 | 0.260 | 0.207 |
| | 825 | −0.043 | 0.207 | 0.158 | −0.018 | 0.121 | 0.075 |
| | 851 | −0.051 | 0.252 | 0.197 | 0.043 | 0.280 | 0.141 |

Virus Neutralization Test (VN Test)

Figures 13, 14:
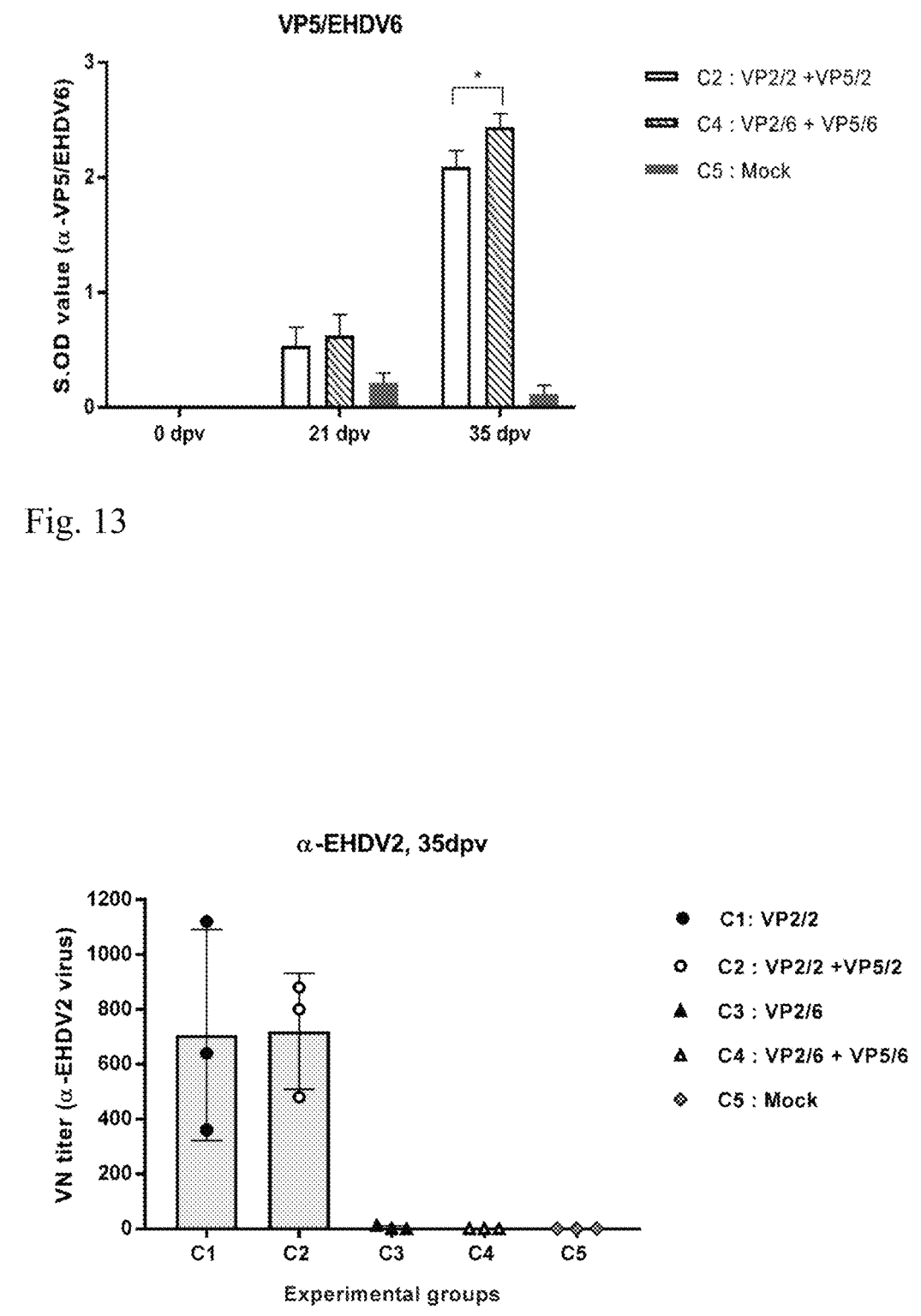

The virus neutralization test was done as described above in the VN section for the mice experiment. Virus neutralization assays against EHDV2 showed high neutralizing titers in serum from cattle immunized with VP2/EHDV2 protein (Group C1) and VP2/EHDV2+VP5/EHDV2 protein (Group C2) at 35 dpv. (FIG. 14 and Tables 11, 12). Some low serum neutralization titers against EHDV2 were detectable on 21 dpv after one dose immunization. Sera from cattle, immunized with VP2 of EHDV6 (Group C3) or with combination of VP2+VP5 of EHDV6 (Group C4) did not show any anti-EHDV2 neutralizing activity. Similarly to the mice studies, there was no cross-neutralization reactivity between EHDV2 and EHDV6 serotypes.

TABLE 11

VN titer of serum against EHDV2 virus
VN titer against EHDV serotype 2 virus (Mean ± SD)

| DPV | C1: VP2/2 | C2: VP2/2 + VP5/2 | C3: VP2/6 | C4: VP2/6 + VP5/6 | C5: Mock |
|---|---|---|---|---|---|
| 0 | 0 | 0 | 0 | 0 | 0 |
| 21 | 10 ± 16.0 | 0 | 0 | 0 | 0 |
| 35 | 706.7 ± 384 | 720.0 ± 2114.2 04.2 ± 7.0 | 4.2 ± 7.0 | 0 | 0 |

TABLE 12

VN titer of individual animal against EHDV 2 virus

| | | VN titer against EHDV 2 | | |
|---|---|---|---|---|
| Group | # cattle | 0 dpv | 21 dpv | 35 dpv |
| C1: VP2 | 677 | 0 | 0 | 1120 |
| | 709 | 0 | 30 | 360 |
| | 743 | 0 | 0 | 640 |
| C2: VP2/2 + VP5/2 | 712 | 0 | 0 | 800 |
| | 794 | 0 | 0 | 480 |
| | 800 | 0 | 0 | 880 |

TABLE 12-continued

VN titer of individual animal against EHDV 2 virus

| | | VN titer against EHDV 2 | | |
|---|---|---|---|---|
| Group | # cattle | 0 dpv | 21 dpv | 35 dpv |
| C3: VP2/6 | 714 | 0 | 0 | 0 |
| | 792 | 0 | 0 | 12.5 |
| | 855 | 0 | 0 | 0 |
| C4: VP2/6 + VP5/6 | 742 | 0 | 0 | 0 |
| | 745 | 0 | 0 | 0 |
| | 779 | 0 | 0 | 0 |
| Mock | 707 | 0 | 0 | 0 |
| | 825 | 0 | 0 | 0 |
| | 851 | 0 | 0 | 0 |

Figure 15:
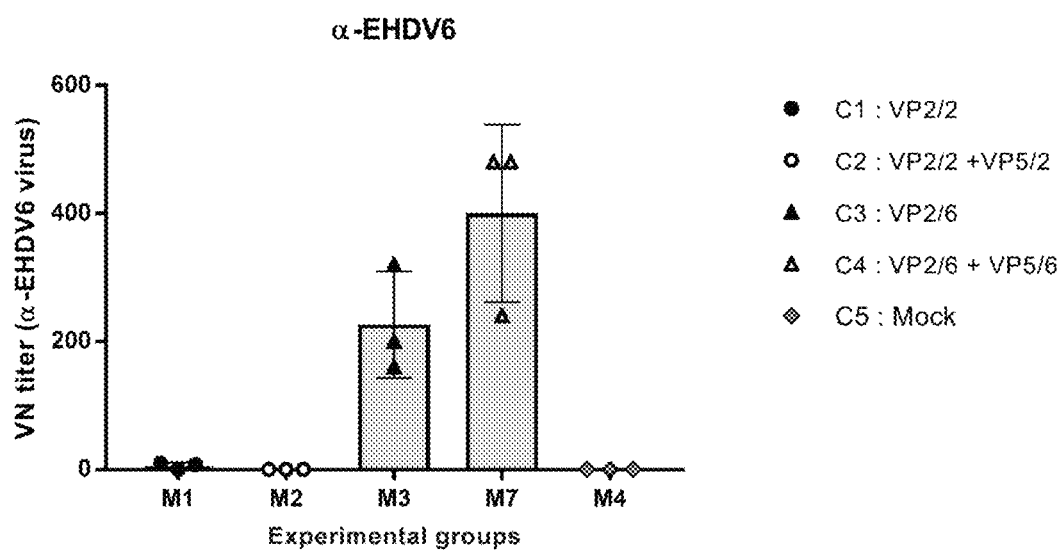
FIG. 15 is a graph illustrating a specific Virus Neutralization titers of serum against EHDV 6 virus at 35 dpv. The individual Virus Neutralization titer presents with mean of respective group with standard deviation.

Virus neutralization assays against EHDV6 showed high neutralizing titers in serum from cattle immunized with VP2/EHDV6 protein (Group C3) and VP2+VP5/EHDV6 proteins (Group C4) at 35 dpv Sera from cattle, immunized with VP2 of EHDV2 (Group C1) or with a combination of VP2+VP5 of EHDV2 (Group C2) did not show any anti-EHDV6 neutralizing activity (FIG. 15 and Tables 13, 14). Some low serum neutralization titers against EHDV6 were detectable on 21 dpv after one dose immunization. Similarly to the mice studies, there was no cross-neutralization reactivity between EHDV2 and EHDV6 serotypes.

TABLE 13

Summary VN titers of serum against EHDV6 serotype (Mean ± SD)
VN titer against EHDV serotype 2 virus (Mean ± SD)

| DPV | C1: VP2/2 | C2: VP2/2 + VP5/2 | C3: VP2/6 | C4: VP2/6 + VP5/6 | C5: Mock |
|---|---|---|---|---|---|
| 0 D | 0 | 0 | 0 | 0 | 0 |
| 21 D | 0 | 0 | 5.8 ± 8.0 | 20 ± 11.4 | 0 |
| 35 D | 5.8 ± 5.2 | 0 | 226.7 ± 83 | 400 ± 138 | 0 |

TABLE 14

VN titers in serum of individual animals against EHDV6 serotype.

| Group | # cattle | VN titer against EHDV 2 | | |
|---|---|---|---|---|
| | | 0 dpv | 21 dpv | 35 dpv |
| C1: 2-VP2 | 677 | 0 | 0 | 0 |
| | 709 | 0 | 30 | 10 |
| | 743 | 0 | 0 | 7.5 |
| C2: VP2/2 + VP5/2 | 712 | 0 | 0 | 0 |
| | 794 | 0 | 0 | 0 |
| | 800 | 0 | 0 | 0 |
| C3: VP2/6 | 714 | 0 | 0 | 200 |
| | 792 | 0 | 2.5 | 160 |
| | 855 | 0 | 15 | 320 |
| C4: VP2/6 + VP5/6 | 742 | 0 | 7.5 | 480 |
| | 745 | 0 | 22.5 | 480 |
| | 779 | 0 | 30 | 240 |
| Mock | 707 | 0 | 0 | 0 |
| | 825 | 0 | 0 | 0 |
| | 851 | 0 | 0 | 0 |

RESULTS AND CONCLUSIONS

One aspect of this investigation was to develop a subunit EHD vaccine to protect ruminants from EHDV infection. The recombinant proteins expressed in baculovirus system were used as vaccine antigens. The immunogenicity of expressed EHDV antigens was evaluated in mice and cattle. The VP2 and VP5 genes of US isolates of EHDV serotypes 1, 2 and 6 were expressed to produce recombinant proteins. The specificity of the proteins was confirmed by western blot using polyclonal anti-EHDV serum and anti-histidine antibody. Expressed EHDV serotype 2 and EHDV serotype 6 proteins were tested for immunogenicity in mice and cattle. In the mouse study, 9 groups of five six-week-old mice (CD1) were immunized with 20 μg of either VP2 or VP5 recombinant protein individually or a combination of the two proteins. In the cattle study, five groups of cattle with 3 animals per group were immunized with 150 μg of either VP2 or a combination of VP2 and VP5 recombinant proteins derived from EHDV serotypes 2 and 6. The vaccine candidates were administrated subcutaneously twice at an interval of 3 weeks. The EHDV specific immune responses in serum from immunized mice and cattle were evaluated using an indirect ELISA and virus neutralization tests. The ELISA results revealed that EHDV-specific antibodies were produced against each of the immunogens. Virus neutralization assays showed the presence of neutralizing antibodies in sera from mice and cattle immunized with VP2 alone, and in sera of mice and cattle immunized with a combination of both, VP2 and VP5 recombinant proteins of both EHDV serotypes (2 & 6).

The results indicate that the recombinant protein VP2 alone and a combination of recombinant proteins VP2/VP5 can elicit neutralizing anti-EHDV antibody responses thus providing protection against EHDV infection; these data support the efficacy of the EHDV vaccine for white tail deer (WTD) and cattle based on baculovirus-expressed EHDV VP2 and VP5 proteins.

What is claimed is:

1. An immunogenic composition comprising:
   at least two VP2 subunits from different serotypes of Epizootic hemorrhagic disease virus (EHDV); and
   at least one component selected from the group consisting of antigens, pharmaceutical carriers, adjuvants, preservatives, stabilizers, or combinations thereof.

2. The immunogenic composition of claim 1, wherein the VP2 subunits are proteins.

3. The immunogenic composition of claim 2, wherein the proteins are expressed using a baculovirus expression system.

4. The immunogenic composition of claim 1, wherein the at least one component is an adjuvant.

5. The immunogenic composition of claim 1, wherein one VP2 subunit from EHDV is the protein expressed by a sequence having at least 95% sequence homology with SEQ ID No. 1 or SEQ ID No. 3.

6. The immunogenic composition of claim 1, wherein one VP2 subunit from EHDV has an amino acid sequence that has at least 95% sequence homology with SEQ ID No. 5 or SEQ ID No. 7.

7. The immunogenic composition of claim 1, wherein one of the at least two VP2 subunits from different serotypes of EHDV is the protein expressed by a sequence having at least 95% sequence homology with SEQ ID No. 1 or with SEQ ID No. 3.

8. The immunogenic composition of claim 1, wherein one of the at least two VP2 subunits from different serotypes of EHDV has an amino acid sequence that has at least 95% sequence homology with SEQ ID No. 5 or with SEQ ID No. 7.

9. A method of reducing the incidence or severity of at least one clinical symptom of EHD, comprising the step of administering an immunogenic composition comprising at least two VP2 subunits and at least one component selected from the group consisting of antigens, pharmaceutical carriers, adjuvants, preservatives, stabilizers, or combinations thereof, wherein the immunogenic composition is the composition of claim 7 or claim 8.

10. The method of claim 9, wherein the clinical symptoms of EHD are selected from the group consisting of loss of appetite, loss of fear of people, weakness, excessive salivation, rapid pulse, rapid respiration rate, fever, lying in bodies of water to reduce body temperature, unconsciousness, blue tongue, head swelling, neck swelling, sloughing or breaking of hooves, lameness, shock, death, and combinations thereof.

11. The method of claim 9, wherein the VP2 subunits are proteins produced using a baculovirus expression system.

12. The method of claim 9, wherein the at least one component is an adjuvant.

13. A method of reducing the incidence or severity of at least one clinical symptom associated with subclinical EHD, comprising the step of administering an immunogenic composition comprising at least two VP2 subunits from EHDV and at least one component selected from the group consisting of antigens, pharmaceutical carriers, adjuvants, preservatives, stabilizers, or combinations thereof, wherein the immunogenic composition of claim 5 or claim 6.

14. The method of claim 13, wherein the symptoms of subclinical EHD are selected from the group consisting of viremia, fever, oral ulcers, excessive salivation, lameness, coronitis, and combinations thereof.

15. The method of claim 13, wherein the VP2 subunits are proteins produced using a baculovirus expression system.

16. The method of claim 13, wherein the at least one component is an adjuvant.

* * * * *

SEQUENCE LISTING

```
<160> NUMBER OF SEQ ID NOS: 8

<210> SEQ ID NO 1
<211> LENGTH: 2949
<212> TYPE: DNA
<213> ORGANISM: Epizootic hemorrhagic disease virus
<220> FEATURE:
<221> NAME/KEY: misc_feature
<223> OTHER INFORMATION: Alberta strain

<400> SEQUENCE: 1
atggaggaga ttttctttag cgtcattgat agcagccagc tcataccgaa acaactatat      60
gaaaattatc ctgtcgttat tgatgtcggg catcggaaaa acgagggtag attgccagtg     120
gaacggctag aagataagca caccatagaa ttaatccaag cggaagcgag aaatctattt     180
tcgtatgaat caaaggagga ttatggagtc atctttccgg atgcgctgtc gattggtata     240
cgcagatatg actggagacg tgcggaatat tctaagaacc agagcgtgga aagaagtaat     300
ggaattatat cgtcggagga tgcgttcgaa gaattaatac gtagctcaag cgcaaatgtg     360
aagttaaaga ctgatttcag tggtggccgt atacatcatg aactgtcata ttgcgatatt     420
cacacagatg caacgatagc agaaaccatc gagatcgatg cgcataataa tgaagaagag     480
ggctgttttc atggtgaaaa tacggtggta tataaccatt tattaacaga gtcgaattac     540
atagggtcgg ggacgtgtta tgacttgggg gatcatatac agctgagaac gataggagac     600
gtcggtccac gacctcgcga tcacgtagac gtattagggc ggacacaccc tagaggagag     660
aagcatataa ttcggagata tggaggtgat gagatcaaaa cactaactac tagtatgagc     720
ccagatgaat ttgaacttaa gaagaaaata cttaatgggg atgtggcgat aggggtagag     780
aaaagaaatt taattaaata tagtaatgag atactacaat tagatgatat tgcggcgagt     840
```

```
tggattagga gccagaacgc gaatgatttg gagaaaattg tcgcattatt agagcggctg    900
ggagaaaaag atcaaaaagt agagccacat aattcgaatg atatacgtga acgctttaga    960
aggaagctgc tccaaaattt acaaaaaacc gacggcgaaa tacgaaatat aaggaattat   1020
catcagcagg atgcgacaaa acgcttcgcg gcagtattga ttgtaaccat gtgtgacaca   1080
atgaaccgcg ctatttgggg agacaataga ttcaagttag tgagggtgt gtatgaatat    1140 gcgaaatata gaatgggatc aatctattat tcaatgcgga cagatgtgac gtggcagttg   1200
cgaacaagct acgtggatgc atgcccgcgc atttgtgatc gaaggagata cataatgcaa   1260
cgatatgact acttctctct gaatcgtgag acgggagatt cgatatataa gtgggatgtg   1320
ggagacatac gtggcggtaa gaaaacatca cgatgggaag gatggccata taaatcaatt   1380
gaagatgaag aagaggacga gaggtatta atacatgatt tcgacgagga taaatatact    1440
caatatatgc aaagagtaat tcagggacct tgggtagaaa aagatgggat cggagtattg   1500
atgaaagagg aggcagccat tgaactattt gattttacac gggacgcgta cgttgacgag   1560
gcaggcttct tgagattgcc tgcgtattat aataaaacaa ttaaatcatc gttgtatgag   1620
tcatccttta agataagacg ggtcgagatc atgcatggga aaaaagccga tccttggact   1680
aaaaagacaa atgacgaatt aaagaaagag aatgagatgt ggcttcttcc tctaccgacg   1740
gtggtggata aaactctatg cttaaccggt aatatcttga gcacaattaa acaggagcaa   1800
agtgctcgat tcactgcgat aatagaagca ttaagaagg aaaagagat agttaagaga    1860 aaatatacgc gtgatgacac ttatacctgc cctatgttaa atgtattgaa ttatacgggg   1920
tatagacagc ggagattcat cttctcgatc ttaaagaacc atctaccgaa agatttactg   1980
atggaggtat atcaggatcc ggatgaagag tatgaccctc atgattacac ggattgcatg   2040
gggaaagaag aagtgttggt cgggatgaga tctatatttg aagtcatact ctatttgatc   2100
catctgggtt tcgaaaatca aatcacaacc tatagcgagg aggagatccg agtgataaaa   2160
cacaggatga tcaagaaaga gcatcgagat ggaatagtgg acatactagc tccaaatttc   2220
tcaagaatca taagagagaa tgaaagatg ataaagatcg agaagtatga agatttattg    2280
ccaatgtact tttatcaagc attggtgcta tcaaacgaaa tgatttacga gaatatgaat   2340
aaatcccacc cgatgttaat gttctgtgat aatagagtca gaattgtccc agtccaaaca   2400
aattcatgga ggaaaagtgt acctctatta tccacacttt ttattttaaa atattatgcg   2460
gggtggcgta agcgggaaga aacgattgaa gatgacatcc gaactgtatg ccacatctg    2520 accagatatt ggttagatgt agaattccag cggagggaaa tcgctgacgg gacggtgata   2580
aggatgcagc cgttgaaaac gcatctaagt acatattgct cgtatatgtc ggaagtctac   2640
agctttgcgt tacccattgt gcatcctaca aaggtataa ttgcggtggg tgtaataccg    2700
gacgtgatct cgaatgcgca aggattttca ataattaagc aaaggtttta ttcaatcgat   2760
cgttacgtgc acgcgagggt gatccttaga atacaaaagg atggcagcgt aaatgtgtac   2820
ggtgaggggg acattaaatg taacgtatta gacaaattct gttgtgggaa gagacgaag    2880 attattagag tgaggcttaa cgggaaagta tacgcgaacc cggaaataat ctcaaagctt   2940
atgaactag                                                           2949
```

<210> SEQ ID NO 2
<211> LENGTH: 1584
<212> TYPE: DNA
<213> ORGANISM: Epizootic hemorrhagic disease virus
<220> FEATURE:
<221> NAME/KEY: misc_feature
<223> OTHER INFORMATION: VP5 subunit

<400> SEQUENCE: 2

| | |
|---|---:|
| atgggcaaga tcatcaagaa attaagtaag gttggaaaaa agataggggga tgctttaacg | 60 |
| tcgaacaccg cgcaacggat ttataaaacg attgggaaag cagcagaacg tttcgtggag | 120 |
| agcgatattg gatcggcggc aatagatggg ttgatacaag gcaccgtaca atcagtcatt | 180 |
| acaggagaat cgtatggaga gaccgttaag caggcggtac tgttaaacgt actcggagcg | 240 |
| ggagatccaa tacctgatcc tttaagccca ggggaacggg gaatgcagac caagattcag | 300 |
| gagttggagg atgaggagag aggtaacacg atacgattaa gacataatga tcggatcttg | 360 |
| aagctatttg ggagagactt agatgatgtg tataacttcg caacggccca aatcgctgag | 420 |
| gatgagttaa aggatgacca gtacgaggtt ttagaaaaag cagtgaagtc ctacggtaaa | 480 |
| gtgatcggag aggaagaacg aagattaaag cagctcaagg atgcactaca gaaggagata | 540 |
| tccgatagaa gtaaaaacga aaagagatg gtggcggaat atcgcaacaa aattgaggcg | 600 |
| ttacgtggag caattgaggt tgaatcagag agtatgcaag aagaggctat acaggaaatc | 660 |
| gcaagcatga gcgctgaaat attagaagca gcctcagaag aggtaccatt ttttggggca | 720 |
| ggcatggcta ctgcaatagc ttcggctaga gcggtggagg gcggatataa gttgaagaag | 780 |
| gtaatcaacg ctctgagcgg aatcgactta agccatctga aacgcctag aatcgaaccc | 840 |
| caaacgttgg aggcgatatt gagaacgcca gcggagttg aaatagcga taccaaactt | 900 |
| gtgactggaa ttgtagcgaa gatcgaagcg gtagaggata tcatcatga gttgaacat | 960 |
| attgaaagac aaatactacc acaaataaag caggcgatga agaggatca cgaagcaata | 1020 |
| ggaagcgaga atacaaagag aatactacca aaaaccgcaa tgcgcttta agtgccattg | 1080 |
| agccagcagc cacagataca tatatatgca gcgccatggg attcagatga cgtgtttata | 1140 |
| ctacattgcg tggcgtcaca tcatgcaaac gagtcatttt ttatggggtt cgatcttgag | 1200 |
| ttagaatatg tcttttatga ggatctgaca cgccattggc atgcactggg tggcgctcag | 1260 |
| gaagcgactg gtagaacttt tcgagaagca tatagagagt ttttctcgtt agcattacag | 1320 |
| caggaagggg cgagcctaat acaccaacgt agactcgctc gttcacgggg tgcgcatccg | 1380 |
| atttacttag gtgccactca ctatgaagtc tcctatgcac agttgaaacg aaatgcattg | 1440 |
| aaattagtaa atgataccga attgcagata catgtgttgc gagggccgaa gcatttccag | 1500 |
| aggcgcgcaa ttatgggagc tatcaaggta ggtgtaagct tacttgggga gattgatttg | 1560 |
| cccgagttta tgcgttacgc gtga | 1584 |

<210> SEQ ID NO 3
<211> LENGTH: 2919
<212> TYPE: DNA
<213> ORGANISM: Epizootic hemorrhagic disease virus
<220> FEATURE:
<221> NAME/KEY: misc_feature
<223> OTHER INFORMATION: VP2 subunit, USA isolate

<400> SEQUENCE: 3

| | |
|---|---:|
| atggaaagcg ttgagttcgc cataataaac aaacaacagc agcctgatga gagtatcata | 60 |
| tatgattatt tgacgacgat acagacgaga acgtatgatg gaagcttag ggcaaggta | 120 |
| gaacgtatga ttaataagaa tacgatagaa ttaacacaag gagaggcccg taattttta | 180 |
| gatcgtgcta ttggtgacga atatcgaatc aatttcccag acgcgttaa ttatggcata | 240 |
| atgagatacg ataatgagca tgaacgctat aacgaaaagg gtgtgatgct attagaacac | 300 |

```
gttaaaccag tggaagagta cgagataatg ttacgaacgt ctatcggcca ccaaaggatt    360
aaaccagagt atggaactca gaacgcacgc ataacttttc tattctcagg tggcgatctc    420
cggatccatt cgaaatttgt tgaaagtttg aagtttgaga ttgtgaacta cgaaacggag    480
gattgcgacc acacacggtg gagaataaat tacgacatga ttctagaggg cggtttgatg    540
ataggttccg gcacatgcta cgatctccta aaacagttag aattgattgt aataggagag    600
attaagcctt caacacggga acgccaaaat gtcataactc ggcagatgat accgatagga    660
acgcctgaaa taacgaacag ggagccttat aaaaataagc aaacaaaaat ccaggcggct    720
ttgggtccaa gagttaatga attgaaaaaa gagattttct ccggaaaata tggtttagaa    780
gttaagcatg tagcaaggtt attggatgat ccgctaataa cacgattaga tgtaattgca    840
gaagagtgga tgcagaggca aagtgacggg aaagtagatg aactttgtga cctcttagaa    900
gctaagggaa gacaaattaa aatggctgga acgagtgcgg actactgtaa aaggcgcga    960 tcacgtttac atggtgtctt gaaagcgaac ttagtcaaga ccaccgatga gattgggaac   1020
atacgcgctg taaaaaatga aaacgcgggg agcattttag ctgcggtact cgtaataagc   1080
gcgtgcgatt cgcagaaaag agcaatttgg tacaatgatg atagcccgat ttatagaggc   1140
attatgttat atgctactga gaagtttggg agcgtgtatt atggattgcg gaggagattt   1200
acgtggtcaa tccgtccgac atacgttgat agttgcccaa gggtatgcga tcgccgacaa   1260
acattcatga cccgaattcc atattttgat ttaaatcaag aagaaggaga ctcaatatac   1320
aaatggaatt tagagccaat actacgagac gtaaagacca ctaggatgga tggatcccca   1380
tatgaagcat atgatggtga tgatgaagac gcgggtttgg tgcatgacat agaccaacgg   1440
aaatatcgcg agatgatcca acgtataatc gacaacgaat ggcaagagaa ggatgggatc   1500
gcaacgataa tatcagatgt aggtggtata gagaaatacg atttcacaaa agatgcatat   1560
atagatgagg cgggatttat aaagttacca gattactacg gaaaacaaat taggtcgaaa   1620
ttatatgggt atagctttga aattactaga gtgtcgatta cagcttcaaa aacagaggat   1680
ccttggcacc aaaaaaccgg aggaaagcta ataaatgagg gtgagttatg gagagttcct   1740
ttggataaca tcattgatgt aacacaatgt ctaagtggaa gagcgataag cgatgttaaa   1800
caaaagagga gcgtaaggtt tgatgaatta ttggaagaag atgaagatgg tgagaatggt   1860
gaatgtgtcc aaaagtatgt tctaggaaaa ataagaaaga aattattcac ccgagttttc   1920
tcaatattga aatggtattt cccaacggaa tatattgaca gtttaattgg ggaggatgag   1980
tacgtatatg acacagagac gtttaatgat attttcaatg aggacggatt tatagacgag   2040
caacaaagtt tgagttctat ggtttttatcc atgatcatca gagcatataa ggatgagcag   2100
gtggatgaac ttcggaacag tacgacctat ctctacagaa tgacagaacg tcgaggcaaa   2160
gagcgagaga cattcttaaa aaagtcgatg ccgaagttct acgcaaaaat tctaaaggtt   2220
cgggaagctg aaaaagttga ggacattcta ccattcattt tcttgcaagc cttattgacg   2280
tcaattgatc accagaaatt ggataaacga gtcagcttac cattctttttt attctgtaaa   2340 gaagaagagc gagtcatacc tgtcagtttt aaagatagct tgatcccgtt gcctttattg   2400
caggtgttac atataatgcg gtttcacccg ggcgaagaga gacgccggaa gcaagtagga   2460
gctgaagtta agaaatcttt acctaaattg ttagattttt ggttcaactt tgcttatgac   2520
aggaaagcat tagacgcggt tgaacatatt agtgaacagt acgtaaagaa tattgtttgc   2580
agctattgtg gaggcaacga ggtagtcgct agcttcatat tgccgatcac ccatccaaaa   2640
aaaggtttta tagtggtgat cgccacaacg gaagatgtcg ctaacagcaa cgcagaggct   2700
```

```
atcgtaaaat caagatttgg cgaggttgca aaatatataa agggagttgt acatataagt    2760
atcacacagg atggagtcgc gcgggttcgc ggtggtggag gaataaagag tcggatatta    2820
gaaaaagttg ttcttggaac acgattccaa ctagtacaaa taaagatggg cgaaaatgtt    2880
tttgaaaatc acgaattagt gacaaagctt atgaattga                          2919
```

<210> SEQ ID NO 4
<211> LENGTH: 1584
<212> TYPE: DNA
<213> ORGANISM: Epizootic hemorrhagic disease virus
<220> FEATURE:
<221> NAME/KEY: misc_feature
<223> OTHER INFORMATION: VP5 subunit

<400> SEQUENCE: 4

```
atggggaaaa ttatcaaaag actcagcaaa tttggaaaga gggtaggcga tgctttcacc      60
tcgaccaccg cacagaaaat ctataagact ataggaaaag ccgcggagag atttgcggaa     120
agcgagatag gatccgctgc gatagatgga ttgattcagg ggagtgtgca gtcgttagtt     180
acaggtgaat cttacggtga aagcgtcaag caggctgtct tactcaatat tctaggagcc     240
ggagatgatg tcccagatcc attaagtccg ggtgaaaggg gattgcaaca taagatccgt     300
gaaatagagg aagagaaaa aggagatcaa ataagattac ggcacaatgc gaagataata     360
gagctatttg ataaagacct tgaagacgtt tacaaatttg cgacggctca gattgacgat     420
gatattatga agaaaaacca gtacgatatt ttagaaaaag cggtgaaatc atatggaaaa     480
gtaataggaa agaggaaga gaaacttcat gatttaacgg ttgccttacg aaaggaggtg     540
gatgacagaa cgcagaacga gagggcgatg gtgggcgaat atcgcaataa gattgacgct     600
ttaaggagcg ctatagaaat agagtcgagg ggaatgcaag aagaggcaat acaggaaata     660
gctggcatga gtgccgatat actcgaagct gcatcggaag aagtaccgtt ctttggcgct     720
ggaattgcaa cagcaatcgc atcagcacgc gcgatagaag gaggatataa gctgaaaaaa     780
gttatcaacg cttttaagcgg tattgactta agccacctaa ggacgccgaa aatacaacct     840
aaaactttgg aagcgatctt aagaacgccg cgtggtgaga gtgtacagga tgtatcgttg     900
gtcgaaggtg taatggcgaa actggaaaca gtgcaaaata actgtaaaga agttgcacac     960
atagaacagc agatttttgcc acagattaag aaggctatta aggaggatca cgaagctata    1020
ggaagtgagg aggagacgag aatattacca gtgaccgcga tgcgttttaa gatcccaatg    1080
tcacagcagc cacagataca catctattcc gcaccttggg attcagatga tgtgttcatg    1140
ctgcattgcg tcgcgcccca ccatataaat gagtccttct tcattgcttt tgatttagag    1200
ctggaatttg tacattttga agacttggcg agacattggc atatattggg aagcgtgcaa    1260
gagccggtag ggcgcacgtt cagagaagcc tataaagaat tttttcaaat agcggttcaa    1320
caagagggcg catcgttgat acaccagaga cgattaatgc gttcacgagg ggttcacccg    1380
atttacctag gggcggtgca ttatgaagtt tcatataggg agttaaagca aaacgctcta    1440
aagttggtta atgattcgga tctacaggcg cacgttctaa ggggcccgaa acatttccaa    1500
cggagagcaa taatgggagc tataaaaatgt ggagtttccc tgctgggaga agtgaatatt    1560
cccgaatttc tgcgctacgc gtga                                           1584
```

<210> SEQ ID NO 5
<211> LENGTH: 982
<212> TYPE: PRT
<213> ORGANISM: Epizootic hemorrhagic disease virus -continued
<220> FEATURE:
<221> NAME/KEY: MISC_FEATURE
<223> OTHER INFORMATION: Alberta strain, VP2 subunit

<400> SEQUENCE: 5

```
Met Glu Glu Ile Phe Phe Ser Val Ile Asp Ser Ser Gln Leu Ile Pro
1               5                   10                  15

Lys Gln Leu Tyr Glu Asn Tyr Pro Val Val Ile Asp Val Gly His Arg
            20                  25                  30

Lys Asn Glu Gly Arg Leu Pro Val Glu Arg Leu Glu Asp Lys His Thr
        35                  40                  45

Ile Glu Leu Ile Gln Ala Glu Ala Arg Asn Leu Phe Ser Tyr Glu Ser
    50                  55                  60

Lys Glu Asp Tyr Gly Val Ile Phe Pro Asp Ala Leu Ser Ile Gly Ile
65                  70                  75                  80

Arg Arg Tyr Asp Trp Arg Arg Ala Glu Tyr Ser Lys Asn Gln Ser Val
                85                  90                  95

Glu Arg Ser Asn Gly Ile Ile Ser Ser Glu Asp Ala Phe Glu Glu Leu
            100                 105                 110

Ile Arg Ser Ser Ser Ala Asn Val Lys Leu Lys Thr Asp Phe Ser Gly
        115                 120                 125

Gly Arg Ile His His Glu Leu Ser Tyr Cys Asp Ile His Thr Asp Ala
    130                 135                 140

Thr Ile Ala Glu Thr Ile Glu Ile Asp Ala His Asn Asn Glu Glu Glu
145                 150                 155                 160

Gly Cys Phe His Gly Glu Asn Thr Val Val Tyr Asn His Leu Leu Thr
                165                 170                 175

Glu Ser Asn Tyr Ile Gly Ser Gly Thr Cys Tyr Asp Leu Gly Asp His
            180                 185                 190

Ile Gln Leu Arg Thr Ile Gly Asp Val Gly Pro Arg Pro Arg Asp His
        195                 200                 205

Val Asp Val Leu Gly Arg Thr His Pro Arg Gly Glu Lys His Ile Ile
    210                 215                 220

Arg Arg Tyr Gly Gly Asp Glu Ile Lys Thr Leu Thr Thr Ser Met Ser
225                 230                 235                 240

Pro Asp Glu Phe Glu Leu Lys Lys Lys Ile Leu Asn Gly Asp Val Ala
                245                 250                 255

Ile Gly Val Glu Lys Arg Asn Leu Ile Lys Tyr Ser Asn Glu Ile Leu
            260                 265                 270

Gln Leu Asp Asp Ile Ala Ala Ser Trp Ile Arg Ser Gln Asn Ala Asn
        275                 280                 285

Asp Leu Glu Lys Ile Val Ala Leu Leu Glu Arg Leu Gly Glu Lys Asp
    290                 295                 300

Gln Lys Val Glu Pro His Asn Ser Asn Asp Ile Arg Glu Arg Phe Arg
305                 310                 315                 320

Arg Lys Leu Leu Gln Asn Leu Gln Lys Thr Asp Gly Glu Ile Arg Asn
                325                 330                 335

Ile Arg Asn Tyr His Gln Gln Asp Ala Thr Lys Arg Phe Ala Ala Val
            340                 345                 350

Leu Ile Val Thr Met Cys Asp Thr Met Asn Arg Ala Ile Trp Gly Asp
        355                 360                 365

Asn Arg Phe Lys Leu Val Arg Gly Val Tyr Glu Tyr Ala Lys Tyr Arg
    370                 375                 380

Met Gly Ser Ile Tyr Tyr Ser Met Arg Thr Asp Val Thr Trp Gln Leu
```

```
                385                 390                 395                 400
Arg Thr Ser Tyr Val Asp Ala Cys Pro Arg Ile Cys Asp Arg Arg Arg
                    405                 410                 415

Tyr Ile Met Gln Arg Tyr Asp Tyr Phe Ser Leu Asn Arg Glu Thr Gly
                420                 425                 430

Asp Ser Ile Tyr Lys Trp Asp Val Gly Asp Ile Arg Gly Gly Lys Lys
                435                 440                 445

Thr Ser Arg Trp Glu Gly Trp Pro Tyr Lys Ser Ile Glu Asp Glu Glu
            450                 455                 460

Glu Asp Glu Glu Val Leu Ile His Asp Phe Asp Glu Asp Lys Tyr Thr
465                 470                 475                 480

Gln Tyr Met Gln Arg Val Ile Gln Gly Pro Trp Val Lys Asp Gly
                485                 490                 495

Ile Gly Val Leu Met Lys Glu Glu Ala Ala Ile Glu Leu Phe Asp Phe
                500                 505                 510

Thr Arg Asp Ala Tyr Val Asp Glu Ala Gly Phe Leu Arg Leu Pro Ala
                515                 520                 525

Tyr Tyr Asn Lys Thr Ile Lys Ser Ser Leu Tyr Glu Ser Ser Phe Lys
                530                 535                 540

Ile Arg Arg Val Glu Ile Met His Gly Lys Lys Ala Asp Pro Trp Thr
545                 550                 555                 560

Lys Lys Thr Asn Asp Glu Leu Lys Lys Glu Asn Glu Met Trp Leu Leu
                565                 570                 575

Pro Leu Pro Thr Val Val Asp Lys Thr Leu Cys Leu Thr Gly Asn Ile
                580                 585                 590

Leu Ser Thr Ile Lys Gln Glu Gln Ser Ala Arg Phe Thr Ala Ile Ile
        595                 600                 605

Glu Ala Leu Lys Lys Glu Lys Glu Ile Val Lys Arg Lys Tyr Thr Arg
            610                 615                 620

Asp Asp Thr Tyr Thr Cys Pro Met Leu Asn Val Leu Asn Tyr Thr Gly
625                 630                 635                 640

Tyr Arg Gln Arg Arg Phe Ile Phe Ser Ile Leu Lys Asn His Leu Pro
                645                 650                 655

Lys Asp Leu Leu Met Glu Val Tyr Gln Asp Pro Asp Glu Glu Tyr Asp
                660                 665                 670

Pro His Asp Tyr Thr Asp Cys Met Gly Lys Glu Glu Val Leu Val Gly
        675                 680                 685

Met Arg Ser Ile Phe Glu Val Ile Leu Tyr Leu Ile His Leu Gly Phe
        690                 695                 700

Glu Asn Gln Ile Thr Thr Tyr Ser Glu Glu Glu Ile Arg Val Ile Lys
705                 710                 715                 720

His Arg Met Ile Lys Lys Glu His Arg Asp Gly Ile Val Asp Ile Leu
                725                 730                 735

Ala Pro Asn Phe Ser Arg Ile Ile Arg Glu Asn Glu Lys Met Ile Lys
                740                 745                 750

Ile Glu Lys Tyr Glu Asp Leu Leu Pro Met Tyr Phe Tyr Gln Ala Leu
            755                 760                 765

Val Leu Ser Asn Glu Met Ile Tyr Glu Asn Met Asn Lys Ser His Pro
        770                 775                 780

Met Leu Met Phe Cys Asp Asn Arg Val Arg Ile Val Pro Val Gln Thr
785                 790                 795                 800

Asn Ser Trp Arg Lys Ser Val Pro Leu Leu Ser Thr Leu Phe Ile Leu
                805                 810                 815
```

```
Lys Tyr Tyr Ala Gly Trp Arg Lys Arg Glu Glu Thr Ile Glu Asp Asp
                820                 825                 830

Ile Arg Thr Val Trp Pro His Leu Thr Arg Tyr Trp Leu Asp Val Glu
            835                 840                 845

Phe Gln Arg Arg Glu Ile Ala Asp Gly Thr Val Ile Arg Met Gln Pro
850                 855                 860

Leu Lys Thr His Leu Ser Thr Tyr Cys Ser Tyr Met Ser Glu Val Tyr
865                 870                 875                 880

Ser Phe Ala Leu Pro Ile Val His Pro Thr Lys Gly Ile Ile Ala Val
                885                 890                 895

Gly Val Ile Pro Asp Val Ile Ser Asn Ala Gln Gly Phe Ser Ile Ile
            900                 905                 910

Lys Gln Arg Phe Tyr Ser Ile Asp Arg Tyr Val His Ala Arg Val Ile
        915                 920                 925

Leu Arg Ile Gln Lys Asp Gly Ser Val Asn Val Tyr Gly Glu Gly Asp
    930                 935                 940

Ile Lys Cys Asn Val Leu Asp Lys Phe Cys Cys Gly Lys Lys Thr Lys
945                 950                 955                 960

Ile Ile Arg Val Arg Leu Asn Gly Lys Val Tyr Ala Asn Pro Glu Ile
                965                 970                 975

Ile Ser Lys Leu Met Asn
            980

<210> SEQ ID NO 6
<211> LENGTH: 527
<212> TYPE: PRT
<213> ORGANISM: Epizootic hemorrhagic disease virus
<220> FEATURE:
<221> NAME/KEY: MISC_FEATURE
<223> OTHER INFORMATION: Alberta strain, VP5 subunit

<400> SEQUENCE: 6

Met Gly Lys Ile Ile Lys Lys Leu Ser Lys Val Gly Lys Lys Ile Gly
1               5                   10                  15

Asp Ala Leu Thr Ser Asn Thr Ala Gln Arg Ile Tyr Lys Thr Ile Gly
            20                  25                  30

Lys Ala Ala Glu Arg Phe Val Glu Ser Asp Ile Gly Ser Ala Ala Ile
        35                  40                  45

Asp Gly Leu Ile Gln Gly Thr Val Gln Ser Val Ile Thr Gly Glu Ser
    50                  55                  60

Tyr Gly Glu Thr Val Lys Gln Ala Val Leu Leu Asn Val Leu Gly Ala
65                  70                  75                  80

Gly Asp Pro Ile Pro Asp Pro Leu Ser Pro Gly Glu Arg Gly Met Gln
                85                  90                  95

Thr Lys Ile Gln Glu Leu Glu Asp Glu Glu Arg Gly Asn Thr Ile Arg
            100                 105                 110

Leu Arg His Asn Asp Arg Ile Leu Lys Leu Phe Gly Arg Asp Leu Asp
        115                 120                 125

Asp Val Tyr Asn Phe Ala Thr Ala Gln Ile Ala Glu Asp Glu Leu Lys
    130                 135                 140

Asp Asp Gln Tyr Glu Val Leu Glu Lys Ala Val Lys Ser Tyr Gly Lys
145                 150                 155                 160

Val Ile Gly Glu Glu Arg Arg Leu Lys Gln Leu Lys Asp Ala Leu
                165                 170                 175

Gln Lys Glu Ile Ser Asp Arg Ser Lys Asn Glu Lys Glu Met Val Ala
```

```
            180                 185                 190
Glu Tyr Arg Asn Lys Ile Glu Ala Leu Arg Gly Ala Ile Glu Val Glu
        195                 200                 205

Ser Glu Ser Met Gln Glu Glu Ala Ile Gln Glu Ile Ala Ser Met Ser
    210                 215                 220

Ala Glu Ile Leu Glu Ala Ala Ser Glu Glu Val Pro Phe Phe Gly Ala
225                 230                 235                 240

Gly Met Ala Thr Ala Ile Ala Ser Ala Arg Ala Val Glu Gly Gly Tyr
                245                 250                 255

Lys Leu Lys Lys Val Ile Asn Ala Leu Ser Gly Ile Asp Leu Ser His
            260                 265                 270

Leu Arg Thr Pro Arg Ile Glu Pro Gln Thr Leu Glu Ala Ile Leu Arg
        275                 280                 285

Thr Pro Ala Gly Val Glu Ile Asp Asp Thr Lys Leu Val Thr Gly Ile
    290                 295                 300

Val Ala Lys Ile Glu Ala Val Glu Asp Asn His His Glu Val Glu His
305                 310                 315                 320

Ile Glu Arg Gln Ile Leu Pro Gln Ile Lys Gln Ala Met Lys Glu Asp
                325                 330                 335

His Glu Ala Ile Gly Ser Glu Asn Thr Lys Arg Ile Leu Pro Lys Thr
            340                 345                 350

Ala Met Arg Phe Lys Val Pro Leu Ser Gln Pro Gln Ile His Ile
        355                 360                 365

Tyr Ala Ala Pro Trp Asp Ser Asp Val Phe Ile Leu His Cys Val
        370                 375                 380

Ala Ser His His Ala Asn Glu Ser Phe Phe Met Gly Phe Asp Leu Glu
385                 390                 395                 400

Leu Glu Tyr Val Phe Tyr Glu Asp Leu Thr Arg His Trp His Ala Leu
                405                 410                 415

Gly Gly Ala Gln Glu Ala Thr Gly Arg Thr Phe Arg Glu Ala Tyr Arg
            420                 425                 430

Glu Phe Phe Ser Leu Ala Leu Gln Gln Glu Gly Ala Ser Leu Ile His
        435                 440                 445

Gln Arg Arg Leu Ala Arg Ser Arg Gly Ala His Pro Ile Tyr Leu Gly
    450                 455                 460

Ala Thr His Tyr Glu Val Ser Tyr Ala Gln Leu Lys Arg Asn Ala Leu
465                 470                 475                 480

Lys Leu Val Asn Asp Thr Glu Leu Gln Ile His Val Leu Arg Gly Pro
                485                 490                 495

Lys His Phe Gln Arg Arg Ala Ile Met Gly Ala Ile Lys Val Gly Val
            500                 505                 510

Ser Leu Leu Gly Glu Ile Asp Leu Pro Glu Phe Met Arg Tyr Ala
        515                 520                 525

<210> SEQ ID NO 7
<211> LENGTH: 972
<212> TYPE: PRT
<213> ORGANISM: Epizootic hemorrhagic disease virus
<220> FEATURE:
<221> NAME/KEY: MISC_FEATURE
<223> OTHER INFORMATION: USA isolate, VP2 subunit

<400> SEQUENCE: 7

Met Glu Ser Val Glu Phe Ala Ile Ile Asn Lys Gln Gln Gln Pro Asp
1               5                   10                  15
```

-continued

```
Glu Ser Ile Ile Tyr Asp Tyr Leu Thr Thr Ile Gln Thr Arg Thr Tyr
             20                  25                  30

Asp Gly Lys Leu Arg Gly Lys Val Glu Arg Met Ile Asn Lys Asn Thr
         35                  40                  45

Ile Glu Leu Thr Gln Gly Glu Ala Arg Asn Phe Leu Asp Arg Ala Ile
     50                  55                  60

Gly Asp Glu Tyr Arg Ile Asn Phe Pro Asp Ala Val Asn Tyr Gly Ile
 65                  70                  75                  80

Met Arg Tyr Asp Asn Glu His Glu Arg Tyr Asn Glu Lys Gly Val Met
                 85                  90                  95

Leu Leu Glu His Val Lys Pro Val Glu Tyr Glu Ile Met Leu Arg
            100                 105                 110

Thr Ser Ile Gly His Gln Arg Ile Lys Pro Glu Tyr Gly Thr Gln Asn
        115                 120                 125

Ala Arg Ile Thr Phe Leu Phe Ser Gly Gly Asp Leu Arg Ile His Ser
    130                 135                 140

Lys Phe Val Glu Ser Leu Lys Phe Glu Ile Val Asn Tyr Glu Thr Glu
145                 150                 155                 160

Asp Cys Asp His Thr Arg Trp Arg Ile Asn Tyr Asp Met Ile Leu Glu
                165                 170                 175

Gly Gly Leu Met Ile Gly Ser Gly Thr Cys Tyr Asp Leu Leu Lys Gln
            180                 185                 190

Leu Glu Leu Ile Val Ile Gly Glu Ile Lys Pro Ser Thr Arg Glu Arg
        195                 200                 205

Gln Asn Val Ile Thr Arg Gln Met Ile Pro Ile Gly Thr Pro Glu Ile
    210                 215                 220

Thr Asn Arg Glu Pro Tyr Lys Asn Lys Gln Thr Lys Ile Gln Ala Ala
225                 230                 235                 240

Leu Gly Pro Arg Val Asn Glu Leu Lys Lys Glu Ile Phe Ser Gly Lys
                245                 250                 255

Tyr Gly Leu Glu Val Lys His Val Ala Arg Leu Leu Asp Asp Pro Leu
            260                 265                 270

Ile Thr Arg Leu Asp Val Ile Ala Glu Glu Trp Met Gln Arg Gln Ser
        275                 280                 285

Asp Gly Lys Val Asp Glu Leu Cys Asp Leu Leu Glu Ala Lys Gly Arg
290                 295                 300

Gln Ile Lys Met Ala Gly Thr Ser Ala Asp Tyr Cys Lys Lys Ala Arg
305                 310                 315                 320

Ser Arg Leu His Gly Val Leu Lys Ala Asn Leu Val Lys Thr Thr Asp
                325                 330                 335

Glu Ile Gly Asn Ile Arg Ala Val Lys Asn Glu Asn Ala Gly Ser Ile
            340                 345                 350

Leu Ala Ala Val Leu Val Ile Ser Ala Cys Asp Ser Gln Lys Arg Ala
        355                 360                 365

Ile Trp Tyr Asn Asp Asp Ser Pro Ile Tyr Arg Gly Ile Met Leu Tyr
    370                 375                 380

Ala Thr Glu Lys Phe Gly Ser Val Tyr Gly Leu Arg Arg Phe
385                 390                 395                 400

Thr Trp Ser Ile Arg Pro Thr Tyr Val Asp Ser Cys Pro Arg Val Cys
                405                 410                 415

Asp Arg Arg Gln Thr Phe Met Thr Arg Ile Pro Tyr Phe Asp Leu Asn
            420                 425                 430

Gln Glu Glu Gly Asp Ser Ile Tyr Lys Trp Asn Leu Glu Pro Ile Leu
```

```
                435                 440                 445
Arg Asp Val Lys Thr Thr Arg Met Asp Gly Tyr Pro Tyr Glu Ala Tyr
450                 455                 460

Asp Gly Asp Asp Glu Asp Ala Gly Leu Val His Asp Ile Asp Gln Arg
465                 470                 475                 480

Lys Tyr Arg Glu Met Ile Gln Arg Ile Ile Asp Asn Glu Trp Gln Glu
                485                 490                 495

Lys Asp Gly Ile Ala Thr Ile Ile Ser Asp Val Gly Gly Ile Glu Lys
                500                 505                 510

Tyr Asp Phe Thr Lys Asp Ala Tyr Ile Asp Glu Ala Gly Phe Ile Lys
            515                 520                 525

Leu Pro Asp Tyr Tyr Gly Lys Gln Ile Arg Ser Lys Leu Tyr Gly Tyr
        530                 535                 540

Ser Phe Glu Ile Thr Arg Val Ser Ile Thr Ala Ser Lys Thr Glu Asp
545                 550                 555                 560

Pro Trp His Gln Lys Thr Gly Gly Lys Leu Ile Asn Glu Gly Glu Leu
                565                 570                 575

Trp Arg Val Pro Leu Asp Asn Ile Ile Asp Val Thr Gln Cys Leu Ser
            580                 585                 590

Gly Arg Ala Ile Ser Asp Val Lys Gln Lys Arg Ser Val Arg Phe Asp
        595                 600                 605

Glu Leu Leu Glu Glu Asp Glu Asp Gly Glu Asn Gly Glu Cys Val Gln
610                 615                 620

Lys Tyr Val Leu Gly Lys Ile Arg Lys Leu Phe Thr Arg Val Phe
625                 630                 635                 640

Ser Ile Leu Lys Trp Tyr Phe Pro Thr Glu Tyr Ile Asp Ser Leu Ile
                645                 650                 655

Gly Glu Asp Glu Tyr Val Tyr Asp Thr Glu Thr Phe Asn Asp Ile Phe
            660                 665                 670

Asn Glu Asp Gly Phe Ile Asp Glu Gln Gln Ser Leu Ser Ser Met Val
        675                 680                 685

Leu Ser Met Ile Ile Arg Ala Tyr Lys Asp Glu Gln Val Asp Glu Leu
690                 695                 700

Arg Asn Ser Thr Thr Tyr Leu Tyr Arg Met Thr Glu Arg Arg Gly Lys
705                 710                 715                 720

Glu Arg Glu Thr Phe Leu Lys Lys Ser Met Pro Lys Phe Tyr Ala Lys
                725                 730                 735

Ile Leu Lys Val Arg Glu Ala Glu Lys Val Glu Asp Ile Leu Pro Phe
            740                 745                 750

Ile Phe Leu Gln Ala Leu Leu Thr Ser Ile Asp His Gln Lys Leu Asp
        755                 760                 765

Lys Arg Val Ser Leu Pro Phe Leu Phe Cys Lys Glu Glu Arg
770                 775                 780

Val Ile Pro Val Ser Phe Lys Asp Ser Leu Ile Pro Leu Pro Leu Leu
785                 790                 795                 800

Gln Val Leu His Ile Met Arg Phe His Pro Gly Glu Arg Arg Arg
                805                 810                 815

Lys Gln Val Gly Ala Glu Val Lys Glu Ile Leu Pro Lys Leu Leu Asp
            820                 825                 830

Phe Trp Phe Asn Phe Ala Tyr Asp Arg Lys Ala Leu Asp Ala Val Glu
        835                 840                 845

His Ile Ser Glu Gln Tyr Val Lys Asn Ile Val Cys Ser Tyr Cys Gly
        850                 855                 860
```

Gly Asn Glu Val Val Ala Ser Phe Ile Leu Pro Ile Thr His Pro Lys
865                 870                 875                 880

Lys Gly Phe Ile Val Val Ile Ala Thr Thr Glu Asp Val Ala Asn Ser
                885                 890                 895

Asn Ala Glu Ala Ile Val Lys Ser Arg Phe Gly Glu Val Ala Lys Tyr
            900                 905                 910

Ile Lys Gly Val Val His Ile Ser Ile Thr Gln Asp Gly Val Ala Arg
            915                 920                 925

Val Arg Gly Gly Gly Ile Lys Ser Arg Ile Leu Glu Lys Val Val
930                 935                 940

Leu Gly Thr Arg Phe Gln Leu Val Gln Ile Lys Met Gly Glu Asn Val
945                 950                 955                 960

Phe Glu Asn His Glu Leu Val Thr Lys Leu Met Asn
                965                 970

<210> SEQ ID NO 8
<211> LENGTH: 527
<212> TYPE: PRT
<213> ORGANISM: Epizootic hemorrhagic disease virus
<220> FEATURE:
<221> NAME/KEY: MISC_FEATURE
<223> OTHER INFORMATION: USA isolate, VP5 subunit

<400> SEQUENCE: 8

Met Gly Lys Ile Ile Lys Arg Leu Ser Lys Phe Gly Lys Arg Val Gly
1               5                   10                  15

Asp Ala Phe Thr Ser Thr Thr Ala Gln Lys Ile Tyr Lys Thr Ile Gly
                20                  25                  30

Lys Ala Ala Glu Arg Phe Ala Glu Ser Glu Ile Gly Ser Ala Ala Ile
            35                  40                  45

Asp Gly Leu Ile Gln Gly Ser Val Gln Ser Leu Val Thr Gly Glu Ser
        50                  55                  60

Tyr Gly Glu Ser Val Lys Gln Ala Val Leu Leu Asn Ile Leu Gly Ala
65                  70                  75                  80

Gly Asp Asp Val Pro Asp Pro Leu Ser Pro Gly Glu Arg Gly Leu Gln
                85                  90                  95

His Lys Ile Arg Glu Ile Glu Glu Glu Lys Gly Asp Gln Ile Arg
            100                 105                 110

Leu Arg His Asn Ala Lys Ile Ile Glu Leu Phe Asp Lys Asp Leu Glu
        115                 120                 125

Asp Val Tyr Lys Phe Ala Thr Ala Gln Ile Asp Asp Ile Met Lys
130                 135                 140

Glu Asn Gln Tyr Asp Ile Leu Glu Lys Ala Val Lys Ser Tyr Gly Lys
145                 150                 155                 160

Val Ile Gly Lys Glu Glu Lys Leu His Asp Leu Thr Val Ala Leu
                165                 170                 175

Arg Lys Glu Val Asp Asp Arg Thr Gln Asn Glu Arg Ala Met Val Gly
            180                 185                 190

Glu Tyr Arg Asn Lys Ile Asp Ala Leu Arg Ser Ala Ile Glu Ile Glu
        195                 200                 205

Ser Glu Gly Met Gln Glu Ala Ile Gln Glu Ile Ala Gly Met Ser
        210                 215                 220

Ala Asp Ile Leu Glu Ala Ala Ser Glu Glu Val Pro Phe Phe Gly Ala
225                 230                 235                 240

Gly Ile Ala Thr Ala Ile Ala Ser Ala Arg Ala Ile Glu Gly Gly Tyr

```
                245                 250                 255
Lys Leu Lys Lys Val Ile Asn Ala Leu Ser Gly Ile Asp Leu Ser His
            260                 265                 270

Leu Arg Thr Pro Lys Ile Gln Pro Lys Thr Leu Glu Ala Ile Leu Arg
        275                 280                 285

Thr Pro Arg Gly Glu Ser Val Gln Asp Val Ser Leu Val Glu Gly Val
        290                 295                 300

Met Ala Lys Leu Glu Thr Val Gln Asn Asn Cys Lys Glu Val Ala His
305                 310                 315                 320

Ile Glu Gln Gln Ile Leu Pro Gln Ile Lys Lys Ala Ile Lys Glu Asp
                325                 330                 335

His Glu Ala Ile Gly Ser Glu Glu Thr Arg Ile Leu Pro Val Thr
            340                 345                 350

Ala Met Arg Phe Lys Ile Pro Met Ser Gln Gln Pro Gln Ile His Ile
            355                 360                 365

Tyr Ser Ala Pro Trp Asp Ser Asp Asp Val Phe Met Leu His Cys Val
        370                 375                 380

Ala Pro His His Ile Asn Glu Ser Phe Phe Ile Ala Phe Asp Leu Glu
385                 390                 395                 400

Leu Glu Phe Val His Phe Glu Asp Leu Ala Arg His Trp His Ile Leu
            405                 410                 415

Gly Ser Val Gln Glu Pro Val Gly Arg Thr Phe Arg Glu Ala Tyr Lys
            420                 425                 430

Glu Phe Phe Gln Ile Ala Val Gln Gln Glu Gly Ala Ser Leu Ile His
            435                 440                 445

Gln Arg Arg Leu Met Arg Ser Arg Gly Val His Pro Ile Tyr Leu Gly
    450                 455                 460

Ala Val His Tyr Glu Val Ser Tyr Arg Glu Leu Lys Gln Asn Ala Leu
465                 470                 475                 480

Lys Leu Val Asn Asp Ser Asp Leu Gln Ala His Val Leu Arg Gly Pro
            485                 490                 495

Lys His Phe Gln Arg Arg Ala Ile Met Gly Ala Ile Lys Cys Gly Val
            500                 505                 510

Ser Leu Leu Gly Glu Val Asn Ile Pro Glu Phe Leu Arg Tyr Ala
        515                 520                 525
```